(12) United States Patent
Stephanopoulos et al.

(10) Patent No.: US 9,267,118 B2
(45) Date of Patent: Feb. 23, 2016

(54) METHODS FOR IDENTIFYING BACTERIAL STRAINS THAT PRODUCE L-TYROSINE

(75) Inventors: Gregory Stephanopoulos, Winchester, MA (US); Christine Nicole S. Santos, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1056 days.

(21) Appl. No.: 12/673,587

(22) PCT Filed: Aug. 15, 2008

(86) PCT No.: PCT/US2008/009766
§ 371 (c)(1),
(2), (4) Date: Mar. 7, 2011

(87) PCT Pub. No.: WO2009/025761
PCT Pub. Date: Feb. 26, 2009

(65) Prior Publication Data
US 2011/0151496 A1    Jun. 23, 2011

Related U.S. Application Data

(60) Provisional application No. 60/965,149, filed on Aug. 17, 2007.

(51) Int. Cl.
*C12Q 1/04* (2006.01)
*C12N 9/02* (2006.01)
*C12Q 1/26* (2006.01)

(52) U.S. Cl.
CPC ............ *C12N 9/0071* (2013.01); *C12Q 1/04* (2013.01); *C12Q 1/26* (2013.01); *C12Y 114/18001* (2013.01); *G01N 2333/90245* (2013.01)

(58) Field of Classification Search
CPC .................................. C12Q 1/04; C12Q 1/26
See application file for complete search history.

(56) References Cited

FOREIGN PATENT DOCUMENTS

WO    WO 2007/038564 A2    4/2007

OTHER PUBLICATIONS

T. Lütke-Eversloh et al., "L-Tyrosine production by deregulated strains of *Escherichia coli*", Appl. Microbiol. Biotechnol. 75:103-110 (May 2007).*
UNIPROT Submission; Accession No. Q8KILO; Oct. 1, 2002.
Cabrera-Valladares et al. Expression of the melA gene from Rhizobium etli CFN42 in *Escherichia coli* and characterization of the encoded tyrosinase. Enzyme Microbial Technol. Apr. 2006;38(6):772-779.
Claus et al. Bacterial tyrosinases. Syst Appl Microbiol. Jan. 2006;29(1):3-14.
Della-Cioppa et al. Melanin production in *Escherichia coli* from a cloned tyrosinase gene. Biotechnology (N Y). Jul. 1990;8(7):634-8.
Lagunas-Muñoz. Optimum melanin production using recombinant *Escherichia coli*. J Appl Microbiol. Nov. 2006;101(5):1002-8.
Santos et al. Melanin-based high-throughput screen for L-tyrosine production in *Escherichia coli*. Appl Environ Microbiol. Feb. 2008;74(4):1190-7.
Santos et al. An inverse metabolic engineering approach for tyrosine production in *Escherichia coli*. 2007 AIChE Annual Meeting, Salt Lake City, Utah. Abstract 213a., Nov. 6, 2007.
Santos et al. Development of a melanin-based screen for tyrosine production in *Escherichia coli*. The 234th ACS National Meeting, Boston, MA. Abstract Biot 145., Aug. 21, 2007.
Udenfriend et al. The chemical estimation of tyrosine and tyramine J Biol Chem. May 1952;196(1):227-33.
Waalkes et al. A fluorometric method for the estimation of tyrosine in plasma and tissues. J Lab Clin Med. Nov. 1957;50(5):733-6.
Genbank Submission; NCBI, Accession No. AAM54973.1; Girard et al.; Aug. 14, 2007.
Alper et al., Construction of lycopene-overproducing *E. coli* strains by combining systematic and combinatorial gene knockout targets. Nat Biotechnol. 2005;23:612-6.
Alper et al., Engineering yeast transcription machinery for improved ethanol tolerance and production. Science. 2006;314:1565-8.
Alper et al., Global transcription machinery engineering: A new approach for improving cellular phenotype. Metab Eng. 2007;9(3):258-67.
Badarinarayana et al., Selection analyses of insertional mutants using subgenic-resolution arrays. Nat Biotechnol. Nov. 2001;19(11):1060-5.
Bailey, Toward a science of metabolic engineering. Science. 1991;252:1668-75.
Berry, Improving production of aromatic compounds in *Escherichia coli* by metabolic engineering. Trends Biotechnol. Jul. 1996;14(7):250-6. Review.
Bongaerts et al., Metabolic engineering for microbial production of aromatic amino acids and derived compounds. Metab Eng. Oct. 2001;3(4):289-300. Review.
Bravo et al., Ammonium assimilation in Rhizobium phaseoli by the glutamine synthetase-glutamate synthase pathway. J Bacteriol. Feb. 1988;170(2):980-4.
Flores et al., Pathway engineering for the production of aromatic compounds in *Escherichia coli*. Nature Biotechnol. 1996;14:620-3.
González et al., The mosaic structure of the symbiotic plasmid of Rhizobium etli CFN42 and its relation to other symbiotic genome compartments. Genome Biol. 2003;4(6):R36.
Ikeda, Towards bacterial strains overproducing L-tryptophan and other aromatics by metabolic engineering. Appl Microbiol Biotechnol. Feb. 2006;69(6):615-26. Review.
Jin et al., Multi-dimensional gene target search for improving lycopene biosynthesis in *Escherichia coli*. Metab Eng. 2007;9:337-47.
Klein-Marcuschamer et al., Assessing the potential of mutational strategies to elicit new phenotypes in industrial strains. PNAS. Feb. 19, 2008;105(7):2319-24.
Lütke-Eversloh et al., A semi-quantitative high-throughput screening method for microbial L-tyrosine production in microtiter plates. J Ind Microbial Biotechnol. 2007;34:807-11.

(Continued)

*Primary Examiner* — Rebecca Prouty
(74) *Attorney, Agent, or Firm* — Wolf, Greenfield & Sacks, P.C.

(57) ABSTRACT

The invention relates to high-throughput screens for identifying bacterial strains capable of L-tyrosine production.

8 Claims, 6 Drawing Sheets

(56) References Cited

OTHER PUBLICATIONS

Lütke-Eversloh et al., Perspectives of biotechnological production of L-tyrosine and its applications. Appl Microbiol Biotechnol. Dec. 2007;77(4):751-62. Review.

Neidhardt et al., Culture Medium for Enterobacteria. J Bacteriol. 1947;119(3):736-47.

Nosanchuk et al., The contribution of melanin to microbial pathogenesis. Cell Microbiol. Apr. 2003;5(4):203-23.

Pfleger et al., Microbial sensors for small molecules: development of a mevalonate biosensor. Metab Eng. Jan. 2007;9(1):30-8.

Qi et al., Functional expression of prokaryotic and eukaryotic genes in *Escherichia coli* for conversion of glucose to p-hydroxystyrene. Metab Eng. 2007;9:268-76.

Ruan et al., Cloning and expression of mel gene from Bacillus thuringiensis in *Escherichia coli*. Antonie Van Leeuwenhoek. May 2005;87(4):283-8.

Sariaslani, Development of a Combined Biological and Chemical Process for Production of Industrial Aromatics from Renewable Resources. Annu Rev Microbiol. 2007;61:51-69.

Sprenger, From scratch to value: engineering *Escherichia coli* wild type cells to the production of L-phenylalanine and other fine chemicals derived from chorismate. Appl Microbiol Biotechnol. Jun. 2007;75(4):739-49. Review.

Taft-Benz et al., The C-terminal domain of dnaQ contains the polymerase binding site. J Bacteriol. May 1999;181(9):2963-5.

Wang et al., Cloning and overexpression of a tyrosinase gene mel from Pseudomonas maltophila. FEMS Microbiol Lett. Apr. 1, 2000;185(1):23-7.

\* cited by examiner

METHODS FOR IDENTIFYING BACTERIAL STRAINS THAT PRODUCE L-TYROSINE

RELATED APPLICATIONS

This application is a national stage filing under 35 U.S.C. §371 of international application PCT/US2008/009766, filed Aug. 15, 2008, which was published under PCT Article 21(2) in English, and claims the benefit under 35 U.S.C. §119(e) of U.S. provisional patent application Ser. No. 60/965,149, filed Aug. 17, 2007, the content of which are incorporated herein by reference in its entirety.

FEDERALLY SPONSORED RESEARCH

This invention was made with government support under grant numbers DGE0202745, DGE0645960, and BES0331364 awarded by the National Science Foundation. The government has certain rights in this invention.

FIELD OF THE INVENTION

The invention relates to high-throughput screens for identifying bacterial strains capable of L-tyrosine production.

BACKGROUND OF THE INVENTION

Traditional metabolic engineering has often focused on the rational design of metabolic pathways, relying on extensive a priori knowledge of cellular mechanisms in order to redirect metabolite flow, revise metabolic regulation, or introduce new pathways to achieve a particular phenotype (4). In recent years, however, considerable advances in molecular biology and the growing availability of annotated genome sequences have made combinatorial methods of metabolic engineering an increasingly attractive approach for strain improvement. With these search strategies, random, traceable genetic-level perturbations are introduced into a cell to yield a new population of strains with a diverse range of properties. A screen is then implemented in order to probe these mutant libraries for strains exhibiting enhancements in the trait of interest. The potential of the combinatorial approach has already been demonstrated for a number of genetic tools and cellular phenotypes. For example, the use of random knockout and overexpression libraries generated via transposon mutagenesis and genomic complementation respectively has led to the isolation of *Escherichia coli* strains with significant increases in the production of the carotenoid lycopene (1, 14). More recently, cell-wide perturbations elicited from global transcription machinery engineering (gTME) has been shown to be effective in improving the tolerance of *E. coli* and *Saccharomyces cerevisiae* to a variety of solvents, including sodium dodecyl sulfate (SDS) and ethanol (2, 3). In each of these examples, the phenotypes of interest could be easily accessed, either by visual selection of red bacterial colonies for the case of lycopene production or a simple growth competition assay for the case of solvent tolerance. For most systems of interest, however, the widespread use of these combinatorial approaches is hampered by the absence of a high-throughput method for selecting strains with the desired cellular properties.

Although L-tyrosine has received far less attention than the other aromatic amino acids, L-tryptophan and L-phenylalanine, it remains a valuable target compound for microbial production. Apart from its use as a dietary supplement, L-tyrosine also serves as a precursor for L-dihydroxyphenylalanine (L-DOPA), a Parkinson's disease drug, and thyroid hormone, used in the treatment of Basedow's or Graves' disease (6). Additionally, L-tyrosine is involved in the synthesis of p-hydroxycinnamic acid and p-hydroxystyrene, both of which serve as starting materials for a variety of novel polymers, adhesives and coatings, pharmaceuticals, biocosmetics, and health and nutrition products (20, 23).

Most prior work on the microbial production of aromatic amino acids has focused largely on two main goals: 1) alleviating the feedback regulation of the product-forming pathway, and, 2) altering central carbon metabolism in order to increase the supply of the two main precursors, erythrose-4-phosphate (E4P) and phosphoenolpyruvate (PEP). The intrinsic regulation of the pathway was disrupted through the deletion of the transcriptional regulator, TyrR, as well as the overexpression of feedback resistant forms of some of the key rate-controlling enzymes. In order to ensure an adequate supply of E4P and PEP, various groups have also tried overexpressing genes responsible for their generation (tktA, talB, pps, pck) and deleting those that deplete the supply of these precursors (ppc, pyrkA, pykF, pts) (5, 6, 13, 24). Although these approaches have certainly led to significant increases in aromatic amino acid production, further gains in yield and productivity may require the modulation of factors that are not directly involved in the biosynthetic pathway or the related precursor forming/utilization reactions. Implementation of the combinatorial metabolic engineering approaches discussed earlier would allow for the identification of these more obscure targets, which may act through unknown or poorly understood mechanisms. A high-throughput screen capable of selecting L-tyrosine-producing mutants from a large, diverse population thus becomes an important tool for the future engineering of these production strains.

For the case of tyrosine production in standard amino acid production host organisms, the current approaches used for measuring tyrosine content in cell cultures, such as High Performance Liquid Chromatography (HPLC) and 1-nitroso-2-naphthol derivatization (26, 27), possess several disadvantages as high throughput screening tools. Although the 1-nitroso-2-naphthol colorimetric/fluorimetric assay can be implemented in a 96-well plate format, the need for strongly acidic reagents and the complexity of sample preparation and derivatization make it an unattractive procedure for testing large numbers of mutants. Despite the sensitivity of HPLC measurements, its low capacity allows for the analysis of less than 100 samples per day, thereby eliminating it as a potential screening tool.

SUMMARY OF THE INVENTION

Here we present the development of a high-throughput screen for L-tyrosine production based on the synthesis of the black and diffusible pigment melanin. This is accomplished through the heterologous expression of a bacterial tyrosinase in the production strain of interest. Tyrosinases, which contain a pair of cupric ions in their active site, use molecular oxygen to catalyze the ortho-hydroxylation of L-tyrosine to L-DOPA, followed by its oxidation to dopachrome. The reactive quinones that are generated then polymerize nonenzymatically to form melanin (9). Tyrosinases are found in a number of phylogenetic groups, and additionally, many bacterial tyrosinases have been shown to have significant activity when expressed in *E. coli* (8, 10, 21, 25). Since melanin is a black pigment with a characteristic absorbance profile, the production of melanin can be easily detected by both visual and spectrophotometric means. Coupling L-tyrosine production and melanin synthesis thus allows for a simple method for identifying high L-tyrosine producers within a mixed population of cells. In this particular study, we have introduced the melA gene from *Rhizobium etli* (8, 15) into a series of *E. coli* L-tyrosine production strains. Strains that either produced or were exposed to greater amounts of L-tyrosine could be distinguished by the unique pigmentation imparted by the synthesis of melanin.

More broadly, the invention provides methods of screening for bacteria that produce metabolites that can be converted by a tyrosinase into a detectable molecule.

The invention also provides a new, more active variant of *R. etli* tyrosinase, nucleic acids encoding the variant tyrosinase, expression vectors including these nucleic acids, and cells containing the variant, the nucleic acid or the expression vector.

According to one aspect of the invention, methods for identifying bacterial strains that produce L-tyrosine are provided. The methods include culturing in a medium one or more bacterial strains capable of L-tyrosine production and which express a tyrosinase, and determining the amount of melanin produced by the one or more bacterial strains. Production of melanin by a strain indicates that the strain produces L-tyrosine. The methods can further include selecting one or more bacterial strains from among the strains that produce melanin. In preferred embodiments, the amount of melanin produced by the one or more bacterial strains correlates positively with the amount of L-tyrosine produced by the one or more bacterial strains.

In some embodiments, the amount of melanin produced by the one or more bacterial strains is detected by a visual method; in other embodiments the amount of melanin produced by the one or more bacterial strains is detected by a spectrophotometric method. In preferred embodiments, the spectrophotometric method comprises measuring optical densities of cell-free culture supernatants at about 400 nm.

In certain embodiments, the one or more bacterial strains are cultured in MOPS minimal medium or M9 minimal medium. In some of these embodiments, the MOPS minimal medium is supplemented with phosphate; preferably the phosphate supplementation comprises $HPO_4^{2-}$. In some of these preferred embodiments, the $HPO_4^{2-}$ is provided by supplementation of the medium with $Na_2HPO_4$ or $K_2HPO_4$.

The methods can be used with different types of bacterial strains. Thus, in some embodiments, the one or more bacterial strains are one or more L-tyrosine production strains. In other embodiments, the one or more bacterial strains are one or more *E. coli* strains.

The tyrosinase expressed by the one or more bacterial strains is a heterologously expressed tyrosinase in some embodiments. In certain preferred embodiments, the heterologously expressed tyrosinase is a *Rhizobium etli* tyrosinase or an active mutant form of a *Rhizobium etli* tyrosinase. An exemplary preferred *Rhizobium etli* tyrosinase is encoded by a melA gene. An exemplary active mutant form of a *Rhizobium etli* tyrosinase is encoded by SEQ ID NO:3. The heterologously expressed tyrosinase can be expressed from a plasmid introduced into the one or more bacterial strains.

In some additional embodiments, the pH of the culture medium is at least about 5, and more preferably is at least about 6.

In certain embodiments, the methods are performed using a liquid medium. Such methods optionally are performed in multiwell plates, preferably in 96 well plates.

In other embodiments, the methods are performed using a solid medium. In such embodiments, the method preferably also includes selecting colonies that exhibit the darkest pigmentation.

The methods identify one or more bacterial strains that produce L-tyrosine. Preferably the one or more bacterial strains are a plurality of bacterial strains from a library. More preferably, the library comprises a plurality of mutations of global transcription machinery.

Once one or more suitable bacterial strains are identified, it may be desired to obtain strain(s) that do not produce the tyrosinase, for example to obtain a L-tyrosine production strain. Thus the methods in some embodiments also include removing the tyrosinase from the one or more bacterial strains after determining the amount of melanin produced by the one or more bacterial strains. If the tyrosinase is encoded by a plasmid, then the step of removing the tyrosinase can include a plasmid curing step. An exemplary plasmid curing step includes culturing selected strain(s) from among the one or more bacterial strains in culture medium that does not contain an antibiotic metabolized by a polypeptide encoded by a plasmid that comprises a gene encoding the tyrosinase. More specifically, where the tyrosinase is encoded by plasmid pTrcmelA$^{mut1}$, the selected strain(s) can be cultured in medium lacking ampicillin or other antibiotics metabolized by the antibiotic resistance gene of plasmid pTrcmelA$^{mut1}$. These embodiments preferably also include verifying loss of the plasmid. In, the methods can also include analyzing L-tyrosine production by the selected strain(s) by culturing the selected strain(s) under culture conditions for L-tyrosine production, and optionally can include collecting and analyzing the L-tyrosine content of the medium. In such methods, the L-tyrosine content of the medium preferably is analyzed by high performance liquid chromatography.

According to another aspect of the invention, additional methods for identifying bacterial strains that produce L-tyrosine are provided that utilize a reporter bacterial strain and one or more bacterial strains capable of L-tyrosine production. The methods include culturing a reporter bacterial strain that expresses a tyrosinase in a sample of a culture medium in which one or more bacterial strains capable of L-tyrosine production are being cultured or have been cultured, and determining the amount of melanin produced by the reporter strain. The production of melanin by a reporter strain indicates that the one or more bacterial strains produces L-tyrosine. The methods can further include selecting one or more bacterial strains from among the strains that produce the samples of culture medium in which the reporter strain produces melanin. In preferred embodiments, the amount of melanin produced by the reporter strain correlates positively with the amount of L-tyrosine produced by the one or more bacterial strains.

In some embodiments, the amount of melanin produced by the reporter strain is detected by a visual method; in other embodiments the amount of melanin produced by the reporter strain is detected by a spectrophotometric method. In preferred embodiments, the spectrophotometric method comprises measuring optical densities of cell-free culture supernatants at about 400 nm.

In certain embodiments, the one or more bacterial strains are cultured in MOPS minimal medium or M9 minimal medium. In some of these embodiments, the MOPS minimal medium is supplemented with phosphate; preferably the phosphate supplementation comprises $HPO_4^{2-}$. In some of these preferred embodiments, the $HPO_4^{2-}$ is provided by supplementation of the medium with $Na_2HPO_4$ or $K_2HPO_4$.

The methods can be used with different types of bacterial strains. Thus, in some embodiments, the one or more bacterial strains are one or more L-tyrosine production strains. In other embodiments, the one or more bacterial strains are one or more *E. coli* strains.

The tyrosinase expressed by the reporter strain is a heterologously expressed tyrosinase in some embodiments. In certain preferred embodiments, the heterologously expressed tyrosinase is a *Rhizobium etli* tyrosinase or an active mutant form of a *Rhizobium etli* tyrosinase. An exemplary preferred *Rhizobium etli* tyrosinase is encoded by a melA gene. An exemplary active mutant form of a *Rhizobium etli* tyrosinase is encoded by SEQ ID NO:3. The heterologously expressed tyrosinase can be expressed from a plasmid introduced into the reporter strain.

In some additional embodiments, the pH of the culture medium is at least about 5, and more preferably is at least about 6.

In certain embodiments, the methods are performed using a liquid medium. Such methods optionally are performed in multiwell plates, preferably in 96 well plates.

In other embodiments, the methods are performed using a solid medium. In such embodiments, the method preferably also includes selecting colonies that exhibit the darkest pigmentation.

The methods identify one or more bacterial strains that produce L-tyrosine. Preferably the one or more bacterial strains are a plurality of bacterial strains from a library. More preferably, the library comprises a plurality of mutations of global transcription machinery.

In some embodiments, the reporter strain is cultured in one or more culture supernatants of the cultures of the one or more bacterial strains. In some of these embodiments, the methods also include selecting strain(s) from among the one or more bacterial strains and analyzing L-tyrosine production by the selected strain(s) by culturing the selected strain(s) under culture conditions for L-tyrosine production, and optionally collecting and analyzing the L-tyrosine content of the medium. Preferably the L-tyrosine content of the medium is analyzed by a high performance liquid chromatography.

In other embodiments, the reporter strain is co-cultured with the one or more bacterial strains. In some of these embodiments, the methods also include selecting strain(s) from among the one or more bacterial strains, isolating the selected strain(s) from the reporter strain, and analyzing L-tyrosine production by the selected strain(s) by culturing the selected strain(s) under culture conditions for L-tyrosine production, and optionally collecting and analyzing the L-tyrosine content of the medium. Preferably the L-tyrosine content of the medium is analyzed by a high performance liquid chromatography.

According to another aspect of the invention, isolated nucleic acid molecules are provided that encode a tyrosinase enzyme of *Rhizobium etli* comprising a base pair substitution in a base pair that encodes the 334$^{th}$ amino acid of a melA gene of *Rhizobium etli*, preferably at the 1000$^{th}$ nucleotide of a melA gene of *Rhizobium etli*, more preferably a C→T base pair substitution.

According to still another aspect of the invention, isolated nucleic acid molecules that include the nucleotide sequence of SEQ ID NO:3 are provided.

According to yet another aspect of the invention, expression vectors that include the foregoing isolated nucleic acid molecule are provided.

According to a further aspect of the invention, bacterial cells that include the foregoing nucleic acid molecules or the foregoing expression vectors are provided.

According to another aspect of the invention, isolated tyrosinase polypeptides are provided. The tyrosinase polypeptides are encoded by a melA gene of *Rhizobium etli* comprising a non-wild type amino acid at the 334$^{th}$ amino acid of the melA-encoded tyrosinase polypeptide, preferably which non-wild type amino acid is serine.

According to still another aspect of the invention, isolated polypeptides are provided that include the amino acid sequence of SEQ ID NO:4.

Also provided by the invention are bacterial cells that include the foregoing tyrosinase polypeptides.

In another aspect, the invention provides bacterial cells identified using the methods described herein that have improved L-tyrosine production relative to a parental strain. In some embodiments, the bacterial cells include one or more mutations. In certain embodiments, the mutation is a mutation of a sigma factor gene, preferably a rpoA gene or a rpoD gene, a dnaQ gene and/or a ygdT gene. In some embodiments, the parental strain is *E. coli* K12 ΔpheA ΔtyrR pCL1920::tyrA$^{fbr}$aroG$^{fbr}$ pTrcmelA$^{mut1}$ or *E. coli* K12 ΔpheA tyrR::P$_{LtetO-1}$-tyrA$^{fbr}$aroG$^{fbr}$lacZ::P$_{LtetO-1}$tyrA$^{fbr}$aroG$^{fbr}$.

These and other aspects of the invention are described further below.

L-tyrosine production of Strains A-E (Table 1) with (black bars) and without (white bars) pTrcmelA$^{mut1}$.

Figure 7:
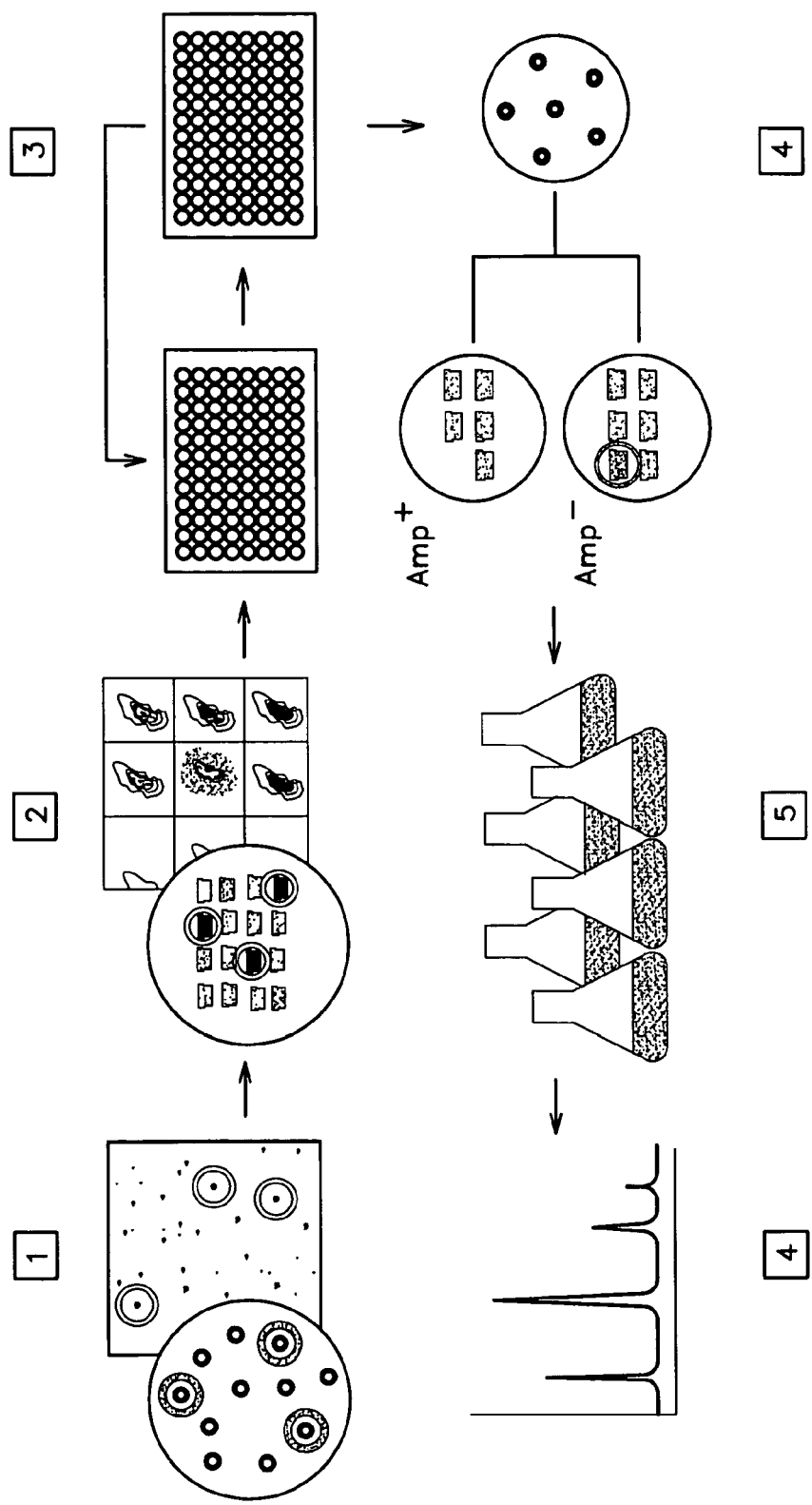

FIG. 7. Strategy for screening libraries on solid media. (1) Plate the library of mutants on MOPS-agar and incubate strains until the melanin pigmentation develops (120-144 hrs). Select the darkest colonies from this first round of screening and (2) streak them out on a fresh set of MOPS-agar plates. Again, incubate plates until the dark coloration develops (120-144 hrs). Select the darkest streaks from this round and (3) proceed to the plasmid curing step. This is achieved by subculturing mutants in Amp⁻ medium at 37° C. to facilitate the loss of pTrcmelA$^{mut1}$. (4) To verify loss of the plasmid, isolate single colonies and check for growth on Amp⁻ and Amp⁺ plates. Strains that now exhibit ampicillin sensitivity are (5) cultivated in the appropriate conditions for L-tyrosine production (MOPS minimal medium, 37° C.). (6) The cell-free culture supernatant is collected and analyzed via HPLC to quantify the L-tyrosine content of the medium. Image brightness and contrast were adjusted with Adobe Photoshop CS2 (Brightness +30; Contrast +30).

DETAILED DESCRIPTION OF THE INVENTION

The invention provides methods for identifying bacterial strains that produce L-tyrosine or other metabolites that can be converted by a tyrosinase to a detectable molecule, such as a pigment. For detection of L-tyrosine, for example, the methods involve culturing in a medium one or more bacterial strains capable of L-tyrosine production and which express a tyrosinase. The amount of the detectable molecule melanin, produced by the one or more bacterial strains, is then detected. By determining the amount of melanin produced by a strain, one can determine that the strain produces L-tyrosine. One or more bacterial strains then can be selected from among the strains that produce melanin.

In some embodiments, the methods employ a reporter strain that expresses a tyrosinase and test strains that are being tested for L-tyrosine production, which does not express a tyrosinase. The L-tyrosine produced by the test strains in the culture medium is converted to melanin by the tyrosinase expressed by the reporter strain; the melanin is subsequently assayed. In such embodiments, the methods include culturing the reporter strain in a sample of a culture medium in which one or more test strains capable of L-tyrosine production are being cultured or have been cultured. Production of melanin by the reporter strain indicates that the one or more test strains produces L-tyrosine. The reporter strain can be cultured in one or more culture supernatants of the cultures of the one or more test bacterial strains. Alternatively, the reporter strain can be co-cultured with the one or more test bacterial strains.

Additional metabolites that can be converted to detectable molecules by tyrosinases are known in the art. For example, see Cabrera-Valladares et al., 2006 (reference 8), which describes conversion of several monohydroxyphenols (e.g., L-tyrosine, L-tyrosine ethyl ester, N-acetyl-L-tyrosine) and dihydroxyphenols (e.g., L-dopa, caffeic acid, catechol) to colored compounds and precipitates. The methods of the invention, described herein for identifying strains that produce L-tyrosine, are also useful for identifying bacterial strains that produce any metabolite that is a substrate for tyrosinase, which produces (directly or indirectly) a detectable product, such as a colored compound or precipitate.

The amount of melanin produced by the one or more bacterial strains (or a reporter strain) correlates positively with the amount of L-tyrosine produced by the one or more bacterial strains. Melanin produced by the one or more bacterial strains (or a reporter strain) can be detected by various methods known in the art, such as visual methods or spectrophotometric methods. In one preferred embodiment, a spectrophotometric method is used that includes measuring optical densities of cell-free culture supernatants at about 400 nm to detect melanin. Additional methods for detecting melanin will be known to the person of skill in the art.

The bacterial strains can be cultured in media of any type (rich or minimal) and composition. The type or composition of media may be the same as the media composition that is to be employed for L-tyrosine production, or may be different, for example to facilitate analysis of melanin visually or spectrophotometrically. Exemplary media for culturing bacterial strains in the methods of the invention include MOPS minimal medium and M9 minimal medium.

The selected medium can be supplemented with various additional components, for example to increase metabolite (e.g., L-tyrosine) production or production of detectable compound (e.g., melanin) by tyrosinase, or detectability of such metabolites or compounds. For example, the working examples show that supplementation of MOPS minimal medium with phosphate enhances the production of melanin. In preferred embodiments, phosphate is supplemented by the addition of $HPO_4^{2-}$, such as by adding $Na_2HPO_4$ or $K_2HPO_4$ to the medium. Other sources of $HPO_4^{2-}$ are also suitable and are well known in the art.

Similarly, other aspects of the medium may be adjusted for carrying out the methods of the invention. For example, the pH of the medium may be adjusted to increase metabolite (e.g., L-tyrosine) production or production of detectable compound (e.g., melanin) by tyrosinase, or detectability of such metabolites or compounds. As shown in the working examples, adjustments to the pH of the medium enhances the production of melanin. The pH of the medium may be adjusted, for example to be at least about 5, at least about 5.5, at least about 6, at least about 6.5, at least about 7, etc.

The methods of the invention can be performed using a liquid medium or a solid medium. When a liquid medium is used, the method can be performed in any of the culture vessels known and used in the art. In one preferred embodiment, multiwell plates (e.g., 24 or 96 well plates) are used for culturing the bacterial strains, which can facilitate parallel processing of cultures for production of L-tyrosine. When a solid medium is used, the method can also include selecting colonies that exhibit the darkest pigmentation, which is indicative of increased melanin production.

The tyrosinase can be expressed endogenously by the bacterial strain(s) being tested (or a reporter strain), i.e., in cases where the strain(s) contains a native copy of the tyrosinase gene that expresses the active enzyme. Bacteria that have endogenous tyrosinases include several species of *Rhizobia, Streptomyces, Pseudomonas*, and *Bacilli*.

The tyrosinase alternatively can be expressed heterologously by the bacterial strain(s) being tested (or a reporter strain). Heterologous expression permits the use of a broader set of bacterial strains because endogenous expression of tyrosinase suitable for conducting the methods of the invention is not required. An active tyrosinase from virtually any species may be expressed heterologously, and the particular tyrosinase used in the methods can be selected based on one or more of a variety of properties of the enzyme, such as optimal temperature or pH of enzyme function. In preferred embodiments, the heterologously expressed tyrosinase is a *Rhizobium etli* tyrosinase or an active mutant form of a *Rhizobium etli* tyrosinase. The *Rhizobium etli* tyrosinase (e.g., accession number AAM54973, SEQ ID NO:2) is encoded by the melA gene (the coding sequence of which is provided herein as SEQ ID NO:1). Alternatively, an active mutant form of a *Rhizobium etli* tyrosinase may be used. An example of an active mutant form of a *Rhizobium etli* tyrosinase is provided herein as SEQ ID NO:4, which is encoded by SEQ ID NO:3.

The heterologously expressed tyrosinase can be expressed from a vector, such as a plasmid, introduced into the one or more bacterial strains (or a reporter strain). A variety of expression vectors can be used for expression of the tyrosinase in the bacterial strains (or a reporter strain). The person of skill in the art is familiar with a variety of vectors that are suitable for expressing enzymes such as tyrosinase in bacterial strains, including reporter strains. Suitable plasmids include plasmids with promoters, including inducible promoters such as the $P_{trc}$ promoter, operably linked to a tyrosinase-coding nucleotide sequence. Exemplary plasmids include pTrcmelA (8), which encodes a *Rhizobium etli* melA tyrosinase, and pTrcmelA$^{mut1}$, which encodes a mutant form of a *Rhizobium etli* melA tyrosinase.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to: plasmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

The tyrosinase can be removed from the one or more bacterial strains after determining the amount of melanin produced by the one or more bacterial strains. This is useful if the bacterial strain is a production strain, in which case the presence of the tyrosinase will not be desirable once the level of L-tyrosine production has been determined. In strains in which the tyrosinase is encoded by a plasmid, removing the tyrosinase can include a plasmid curing step. For example, the plasmid can be cured by culturing selected strain(s) in culture medium that does not contain an antibiotic that is metabolized by a polypeptide encoded by the plasmid. This removes the selective pressure for maintaining the plasmid in the selected bacterial strain(s), which facilitates the loss of the plasmid. Colonies of the strain(s) then can be selected and cultured in parallel in media with and without the antibiotic. Colonies that grow only in media without the antibiotic are bacteria that have lost the plasmid expressing the tyrosinase, and these colonies are preferred for further use in L-tyrosine production. The methods also can include verifying loss of the plasmid by a variety of methods known in the art, such as an inability to amplify the plasmid sequence by polymerase chain reaction (PCR) or a lack of hybridization of nucleic acids from the bacterial strain to one or more probes specific for the plasmid.

In cases where a reporter strain is used, the test strains of interest can be selected, and the selected strain(s) can be isolated from the reporter strain without the need to remove a plasmid or other tyrosinase-encoding nucleic acid from the (potential) L-tyrosine production strain.

The method can also include analyzing L-tyrosine production by the selected strain(s) after removing the plasmid or other tyrosinase-encoding nucleic acid. For example, the selected strain(s) can be cultured under culture conditions suitable for L-tyrosine production, and then optionally the medium can be collected, followed by analyzing the L-tyrosine content of the medium. Any quantitative method of L-tyrosine analysis known in the art can be used, including high performance liquid chromatography.

The methods of the invention are applicable for screening any group of strains exhibiting phenotypic diversity, whether naturally occurring or engineered. Different "libraries" of strains exhibiting phenotypic diversity can be generated in a variety of ways, including by random mutagenesis (by a natural evolutionary process or induced by chemical mutagens), random gene knockouts and overexpressions, global transcription machinery engineering such as are described in PCT published application WO2007/038564, etc. Thus the methods are useful for screening libraries of bacterial strains exhibiting phenotypic diversity to obtain a plurality of bacterial strains that have increased L-tyrosine production capability. In preferred embodiments, the library being screened includes bacterial strains having a plurality of mutations of global transcription machinery.

It may be advantageous to use bacterial strains that are previously optimized for a predetermined phenotype prior to introducing phenotypic diversity. Thus, in the production of L-tyrosine, rather than starting with a bacterial cell that produces only a small amount of L-tyrosine, one preferentially uses a cell that produces a higher amount of L-tyrosine, more preferably an optimized amount of L-tyrosine. In such cases, introduction of phenotypic diversity, e.g., by gTME, is used to further improve an already-improved phenotype.

The bacterial strains used in the methods can be L-tyrosine production strains. Exemplary L-tyrosine production strains include *Corynebacterium glutamicum* and *Brevibacterium lactofermentum*. *E. coli* strains also can be used in the methods of the invention, as production (test) strains and/or as reporter strains. The strains used for L-tyrosine production need not be the same as the reporter strain for methods that employ a reporter strain. It is possible to utilize the methods of the invention for strain optimization, i.e., to determine if alterations made to a strain result in changes in L-tyrosine production. This can be used, for example, to select improved strains having higher L-tyrosine production from among a larger number of strains being developed.

The invention also includes bacterial strains and cells identified by any of the methods described herein. The cells are useful for a variety of purposes, including: industrial production of molecules (e.g., L-tyrosine).

Another aspect of the invention involves the identification of a novel tyrosinase. The novel tyrosinase is an active variant of the tyrosinase encoded by the melA gene of *Rhizobium etli*. During the process of cloning the melA gene of *Rhizobium etli*, the melA gene was amplified and introduced into a plasmid vector under the control of the IPTG-inducible promoter, $P_{trc}$. The sequences of the *R. etli* melA coding sequence are provided as SEQ ID NO:1 (nucleotide sequence) and SEQ ID NO:2 (amino acid sequence). During sequence verification of the plasmid construct, a variant was discovered containing a C→T base pair substitution at the $1000^{th}$ nucleotide of the melA gene, a change which results in a proline to serine switch in the $334^{th}$ amino acid. The sequences of the variant *R. etli* melA coding sequence are provided as SEQ ID NO:3 (nucleotide sequence) and SEQ ID NO:4 (amino acid sequence). This single amino acid substitution led to a significant reduction in the lag time before the onset of melanin production, with the variant tyrosinase showing signs of melanin synthesis 12 hours ahead of the wild-type tyrosinase.

Thus the invention provides isolated nucleic acid molecules encoding a tyrosinase enzyme of *Rhizobium etli* comprising a C→T base pair substitution at the $1000^{th}$ nucleotide of a melA gene of *Rhizobium etli*. The nucleic acid molecules can include the nucleotide sequence of SEQ ID NO:3, or any nucleotide sequence that encodes the amino acid sequence of SEQ ID NO:4.

Isolated tyrosinase polypeptides encoded by a melA gene of *Rhizobium etli* comprising a serine at the $334^{th}$ amino acid also are provided. Preferably the isolated polypeptide includes the amino acid sequence of SEQ ID NO:4.

Vectors including the foregoing nucleic acid molecules also are provided. The vectors can be cloning vectors or expression vectors, as described in more detail elsewhere herein.

Bacterial strains or cells that include the foregoing nucleic acid molecules, polypeptides or vectors (preferably expression vectors) also are provided. The bacterial strains or cells can be strains that produce L-tyrosine or can be reporter strains for use in the methods described herein.

EXAMPLES

Example 1

A Melanin-Based High-Throughput Screen for L-Tyrosine Production in *Escherichia coli*

We present the development of a simple, high-throughput screen for identifying bacterial strains capable of L-tyrosine production. Through the introduction of a heterologous gene encoding for a tyrosinase, we were able to link L-tyrosine production in *Escherichia coli* with the synthesis of the black and diffusible pigment melanin. Although melanin was initially produced only at low levels in MOPS minimal medium, phosphate supplementation was found to be sufficient for increasing both the rates of synthesis and final titers of melanin. Furthermore, a strong linear correlation between extracellular L-tyrosine content and melanin formation was observed using this new medium formulation. A selection strategy that utilizes these findings has been developed and has been shown to be effective in screening large combinatorial libraries in the search for L-tyrosine overproducing strains.

Materials and Methods

Bacterial Strains and Cultivation Conditions

*R. etli* CFN42 was kindly provided by G. Dávila (12) and cultured in Peptone-Yeast extract (PY) medium at 30° C. (7). *E. coli* DH5α (Invitrogen) was used for routine transformations as described in the protocol and cultivated in Luria-Bertani (LB) medium. The following plasmids were transformed into *E. coli* K12 ΔpheA ΔtyrR (T. Lütke-Everslohand G. Stephanopoulos, unpublished data) and/or *E. coli* K12 ΔpheA ΔtyrR ΔwecB (C.N.S. Santos and G. Stephanopoulos, unpublished data) and used for L-tyrosine and melanin production experiments: pCL1920::tyrA$^{WT}$aroG$^{WT}$, pCL1920::tyrA$^{fbr}$aroG$^{WT}$, pCL1920::tyrA$^{WT}$aroG$^{fbr}$, pCL1920::tyrA$^{fbr}$aroG$^{fbr}$, pTrcmelA, and pTrcmelA$^{mut1}$ (16). L-tyrosine production experiments were performed at 37° C. with 225 rpm orbital shaking in 50 ml MOPS minimal medium (Teknova) (17) cultures supplemented with 5 g/L glucose and an additional 4 g/L NH$_4$Cl. Liquid melanin production experiments were performed at 30° C. with 225 rpm orbital shaking in 50 ml M9 (22) or MOPS minimal medium cultures supplemented with 5 g/L glucose, an additional 4 g/L NH$_4$Cl, 40 µg/ml CuSO$_4$, and L-tyrosine at the indicated concentrations. All liquid cultivations were conducted in at least triplicates. Solid melanin production experiments were performed at 30° C. in MOPS minimal medium supplemented with 5 g/L glucose, an additional 4 g/L NH$_4$Cl, 0.4 µg/ml CuSO$_4$, 15 g/L Bacto Agar (BD Diagnostics), and L-tyrosine at the indicated concentrations. When appropriate, antibiotics were added in the following concentrations: 100 µg/ml carbenicillin for maintenance of pTrcmelA and 50 µg/ml spectinomycin for maintenance of pCL1920-derived plasmids. Carbenicillin was chosen in place of ampicillin due to its improved stability during the longer cultivations (>48 hours) required for the synthesis of melanin. Isopropyl-β-D-thiogalactopyranoside (IPTG) was added at a concentration of 1 mM for the induction of pTrcmelA and 3 mM for the induction of both pTrcmelA and pCL1920-derived plasmids. All chemicals, including those used in the supplementation experiments—$CaCl_2$, NaCl, $Na_2HPO_4$, $NaH_2PO_4$, and $K_2HPO_4$—were purchased from Sigma, J.T. Baker, or Mallinckrodt Chemicals.

Construction of pTrcmelA

R. etli CFN42 genomic DNA was extracted with the Wizard Genomic DNA Purification Kit (Promega) and used as a template for the amplification of melA with Pfu Turbo DNA polymerase (Stratagene) and the following primers: melA sense NcoI (5'-TAA ACC ATG GCG TGG CTG GTC GGC A-3'; SEQ ID NO:5) and melA anti Hind III (5'-ACG AAG CTT TTA GGC GGA CAC TAT GGC TAT TTC TAG CTT-3'; SEQ ID NO:6). In order to introduce an NcoI restriction site for cloning, the start codon was changed from TTG to ATG, and the second codon was changed from CCG to GCG. This second alteration resulted in a proline to alanine substitution in the second amino acid. The melA PCR product was digested with NcoI and HindIII and ligated into the NcoI/HindIII-digested plasmid pTrcHis2B (Invitrogen) for one hour at room temperature. The plasmid was transformed into chemically competent E. coli DH5α cells (Invitrogen) and plated on LB-agar plates containing 100 µg/ml ampicillin, 1 mM IPTG, 500 mg/L L-tyrosine and 0.4 µg/ml $CuSO_4$. This latter step was designed to facilitate the selection of clones with correct plasmids, which should synthesize melanin and form dark colonies. Plasmid constructs were isolated and verified by sequencing. All enzymes used in the cloning procedure were purchased from New England Biolabs.

Analytical Methods

For the quantification of L-tyrosine, cell-free culture supernatants were filtered through 0.2 µm PTFE membrane syringe filters (VWR International) and used for HPLC analysis with a Waters 2690 Separations module connected with a Waters 996 Photodiode Array detector (Waters) set to a wavelength of 278 nm. The samples were separated on a Waters Resolve C18 column with 0.1% (vol/vol) trifluoroacetic acid (TFA) in water (solvent A) and 0.1% (vol/vol) TFA in acetonitrile (solvent B) as the mobile phase. The following gradient was used at a flow rate of 1 ml/min: 0 min, 95% solvent A+5% solvent B; 8 min, 20% solvent A+80% solvent B; 10 min, 80% solvent A+20% solvent B; 11 min, 95% solvent A+5% solvent B. For the quantification of melanin, the optical densities of cell-free culture supernatants at 400 nm were determined with an Ultrospec 2100 pro UV/Visible spectrophotometer (Amersham Biosciences) and compared to a synthetic melanin standard (Sigma). For cell density determinations, the optical densities of cultures and cell-free culture supernatants were measured at 600 nm. Since melanin affects the absorbance measurements at this wavelength, the cell density is calculated by taking the difference between these two values. pH measurements were taken with a SymPhony SP20 pH meter and electrode (VWR International).

Library Construction and Screening

Transposon mutagenesis (random knockout) libraries for K12 ΔpheA ΔtyrR pCL1920::tyrA$^{fbr}$aroG$^{fbr}$ pTrcmelA$^{mut1}$ were generated by transformation with 1000-1300 ng of the pJA1 vector (29). After an initial 1-hour outgrowth at 37° C., cells were centrifuged at 2000×g and resuspended in 1 ml MOPS minimal medium. Cells were then plated on 150×15 mm petri dishes containing MOPS minimal medium with 5 g/L glucose, an additional 4 g/L $NH_4Cl$, 40 µg/ml $CuSO_4$, and 20 mM $Na_2HPO_4$. Additionally, the media was supplemented with 10 µg/ml kanamycin to select for strains with transposon-mediated chromosomal integrations. After an incubation period of 120-144 hours at 30° C., 165 of the darkest colonies (representing 7.9% of the total population) were chosen and restreaked on a fresh set of MOPS-agar plates. 30 colonies exhibiting the greatest melanin production after an additional 120-144 hours of incubation were used to inoculate 200 µl of LB medium containing 1 mM IPTG and 50 µg/ml spectinomycin. After four rounds of subculturing, with each round lasting at least 5 to 6 hours, individual colonies were isolated and tested for the loss of pTrcmelA$^{mut1}$ by streaking on Amp$^+$ and Amp$^-$ LB plates. Ampicillin-sensitive colonies were then analyzed for L-tyrosine production under the cultivation conditions described above. A modified Thermal Asymmetric Interlaced PCR (Tail-PCR) protocol was used to sequence and identity promising transposon targets (1).

Results

Isolation of a melA Variant with an Enhanced Capacity for Melanin Synthesis

Figure 1:
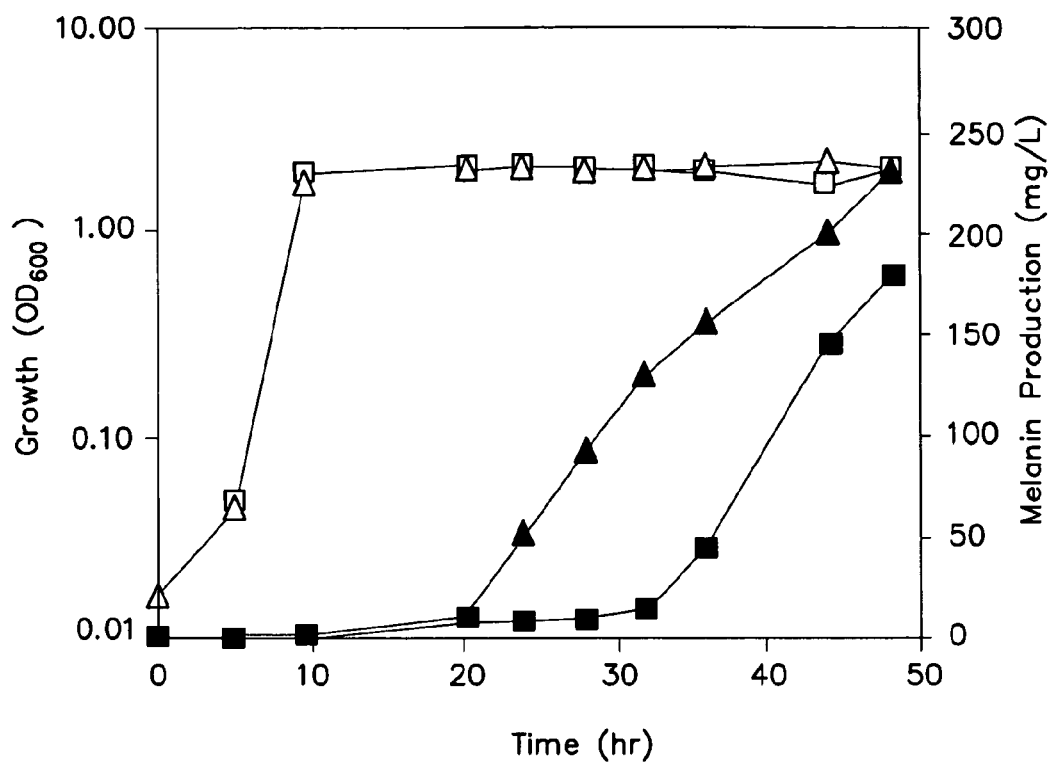
FIG. 1. Growth and melanin production of K12 ΔpheA ΔtyrR expressing two versions of the *R. etli* melA gene. Cultures were grown in M9 minimal medium with 500 mg/L L-tyrosine supplementation. Growth (OD$_{600}$): □, pTrcmelA; Δ, pTrcmelA$^{mut1}$. Melanin production (mg/L): ■, pTrcmelA; ▲, pTrcmelA$^{mut1}$.

The melA gene was amplified from R. etli genomic DNA and introduced into the pTrcHis2B vector under the control of the IPTG-inducible promoter, $P_{trc}$. During sequence verification of the plasmid construct, a variant was discovered containing a C→T base pair substitution at the 1000$^{th}$ nucleotide of the melA gene, a change which results in a proline to serine switch in the 334$^{th}$ amino acid. This single amino acid substitution led to a significant reduction in the lag time before the onset of melanin production, with the mutant showing signs of melanin synthesis 12 hours ahead of the wild-type (FIG. 1). The mutated plasmid variant, named pTrcmelA$^{mut1}$, was therefore selected for use in subsequent melanin production experiments.

Melanin Production in M9 and MOPS Minimal Media

Figure 2:
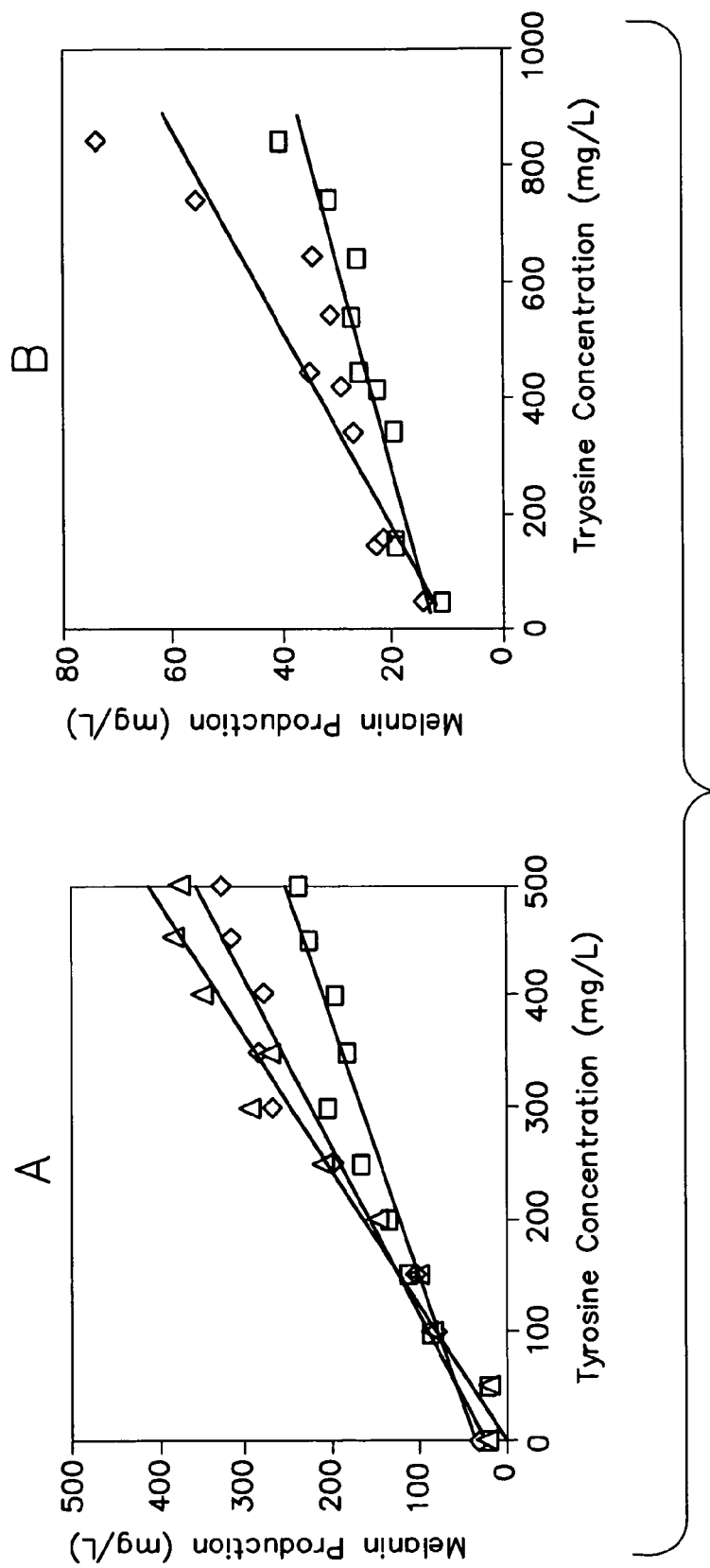
FIG. 2. Correlation between melanin production and external L-tyrosine concentrations in different media formulations. (A) M9 minimal medium—K12 ΔpheA ΔtyrR pTrcmelA$^{mut1}$ was cultivated in 0 to 500 mg/L L-tyrosine in 50 mg/L increments. Melanin measurements were taken after 48 hr (□), 72 hr (◇), and 96 hr (Δ) of cultivation. R$^2$ values for the linear regressions were 0.922, 0.956, and 0.968, respectively. (B) MOPS minimal medium—Five L-tyrosine production strains (Table 1) were transformed with pTrcmelA$^{mut1}$ and assayed for melanin production in media without L-tyrosine supplementation. In order to probe a wider L-tyrosine concentration range, Strain D was also cultivated in medium containing 100, 200, 300, 400, and 500 mg/L L-tyrosine. Melanin measurements are shown after 313 hr (□) and 410 hr (CO) of growth. R$^2$ values for the linear regressions were 0.875 and 0.797, respectively.

In order to demonstrate the feasibility of probing L-tyrosine concentrations through melanin production, K12 ΔpheA ΔtyrR pTrcmelA$^{mut1}$ was cultured in liquid M9 minimal medium supplied with varying amounts of L-tyrosine (0 to 500 mg/L in 50 mg/L increments). As expected, a positive linear trend was observed between extracellular L-tyrosine supplementation and melanin production after 48 hours of cultivation, with a linear regression $R^2$ value of 0.922. Cultures grown with higher concentrations of L-tyrosine (>250 mg/L) continued to produce melanin after this period, leading to even greater resolution and higher $R^2$ values after 72 and 96 hours (FIG. 2A).

Since L-tyrosine production is typically enhanced by as much as fifteen-fold in MOPS minimal medium as compared to M9 minimal medium (data not shown), steps were taken to determine whether these initial results could be reproduced in this alternate medium formulation. Surprisingly, the initial results in M9 minimal medium were not reproducible in MOPS minimal medium. For these experiments, five L-tyrosine production strains (Table 1) were transformed with pTrcmelA$^{mut1}$ and cultivated in media without L-tyrosine supplementation. Additionally, K12 ΔpheA ΔtyrR pCL1920::tyrA$^{fbr}$aroG$^{fbr}$ pTrcmelA$^{mut1}$ (Strain D) was cultured in media containing 100 to 500 mg/L L-tyrosine (in 100 mg/L increments) to extend the range of L-tyrosine concentrations tested. Under these conditions, two significant drawbacks with the use of MOPS minimal medium were encountered—1) the poor resolving power of the assay due to the low levels of melanin produced and 2) the inordinate length of time needed for melanin synthesis to occur. Although a weaker linear correlation between L-tyrosine and melanin concentrations was still observed after 313 and 410 hours (FIG. 2B), the highest melanin titers were five-fold lower than those produced in M9 minimal medium (74 mg/L versus 375 mg/L). Furthermore, a six-fold longer incubation period (313 hr versus 48 hr) was required for this trend to develop.

TABLE 1

Production strains and L-tyrosine titers after 24 hrs

| Strain | Genotype | L-tyrosine production (mg/L) |
|---|---|---|
| A | K12 ΔpheA ΔtyrR pCL1920::tyrA$^{WT}$aroG$^{WT}$ | 47.3 |
| B | K12 ΔpheA ΔtyrR pCL1920::tyrA$^{WT}$aroG$^{fbr}$ | 155.8 |
| C | K12 ΔpheA ΔtyrR pCL1920::tyrA$^{fbr}$aroG$^{WT}$ | 145.9 |
| D | K12 ΔpheA ΔtyrR pCL1920::tyrA$^{fbr}$aroG$^{fbr}$ | 342.0 |
| E | K12 ΔpheA ΔtyrR ΔwecB pCL1920::tyrA$^{fbr}$aroG$^{fbr}$ | 414.0 |

Optimizing Melanin Production in MOPS Minimal Medium

Figure 3:
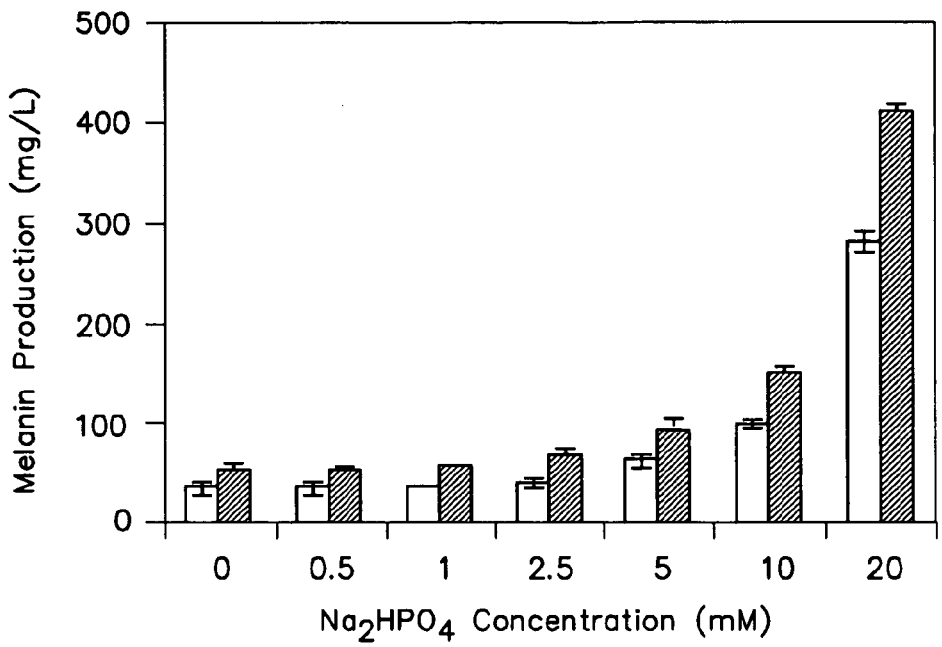
FIG. 3. Melanin production by K12 ΔpheA ΔtyrR pTrcmelA$^{mut1}$ in MOPS minimal medium with different amounts of Na$_2$HPO$_4$ supplementation. All cultures were additionally supplemented with 500 mg/L L-tyrosine. Melanin measurements were taken after 72 hr (white bars) and 96 hr (black bars).

Supplementation experiments were conducted in order to determine which M9 component, if any, could improve tyrosinase enzyme activity in MOPS minimal medium. A comparison of medium compositions revealed that M9 minimal medium contains 180-fold more calcium chloride ($CaCl_2$) and 32-fold more hydrogen phosphate ($HPO_4^{2-}$) than MOPS minimal medium (17); hence, the effects of $CaCl_2$ and sodium phosphate (dibasic, $Na_2HPO_4$) supplementation were examined. Although the addition of 0.09 mM $CaCl_2$ had a slightly detrimental effect on melanin synthesis, $Na_2HPO_4$ at both concentrations tested (40 and 60 mM) was sufficient for restoring melanin production in MOPS minimal medium (Table 2). Melanin concentrations measured after 72 and 96 hours were comparable to those previously observed for M9 minimal medium. In order to minimize the deviation from the standard recipe for MOPS minimal medium, lower concentrations of $Na_2HPO_4$ were also tested for their effect on melanin synthesis. Further optimization of the $Na_2HPO_4$ concentration revealed that only 20 mM was necessary to achieve adequate levels of melanin production (FIG. 3).

TABLE 2

Melanin production of K12 ΔpheA ΔtyrR pTrcmelA$^{mut1}$ in MOPS minimal medium with supplementation $^a$

| Supplementation | Melanin Production (mg/L) | |
|---|---|---|
| | 72 hr | 96 hr |
| None | 72.0 | 96.6 |
| CaCl$_2$ | | |
| 0.09 mM Na$_2$HPO$_4$ | 27.5 | 41.4 |
| 40 mM | 318.6 | 424.8 |
| 60 mM | 337.7 | 349.1 |

$^a$ All cultures were supplemented with 500 mg/L L-tyrosine.

Figure 4:
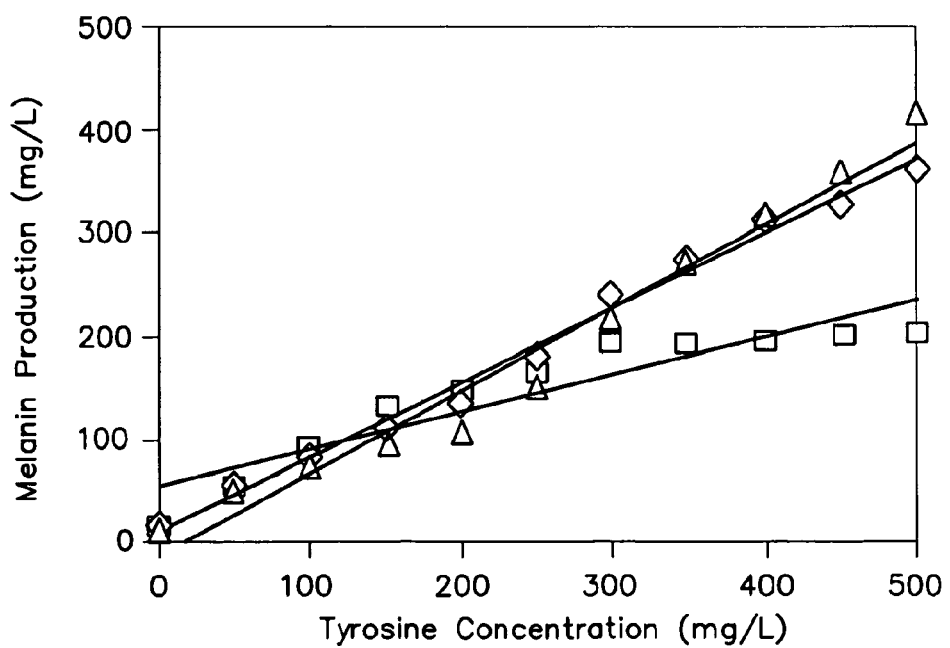
FIG. 4. Correlation between melanin production and L-tyrosine supplementation in MOPS minimal medium with 20 mM Na$_2$HPO$_4$. K12 ΔpheA ΔtyrR pTrcmelA$^{mut1}$ was cultivated in 0 to 500 mg/L L-tyrosine in 50 mg/L increments. Melanin measurements were taken after 72 hr (□), 96 hr (◇), and 120 hr (Δ) of cultivation. R$^2$ values for the linear regressions were 0.853, 0.992, and 0.970, respectively.

To determine whether a correlation between melanin production and L-tyrosine concentration could be established with the optimized medium formulation, K12 ΔpheA ΔtyrR pTrcmelA$^{mut1}$ was once again cultured in varying concentrations of L-tyrosine. In stark contrast to the original MOPS minimal medium experiment, supplementation with 20 mM $Na_2HPO_4$ led to significant increases in the rates of melanin synthesis, as well as final titers of melanin. A linear trend was observed up to 300 mg/L L-tyrosine after 72 hours. After a cultivation period of 96 hours, a strong correlation was seen for the entire range of L-tyrosine concentrations tested, exhibiting a linear regression $R^2$ value of 0.992 (FIG. 4).

Figure 5:
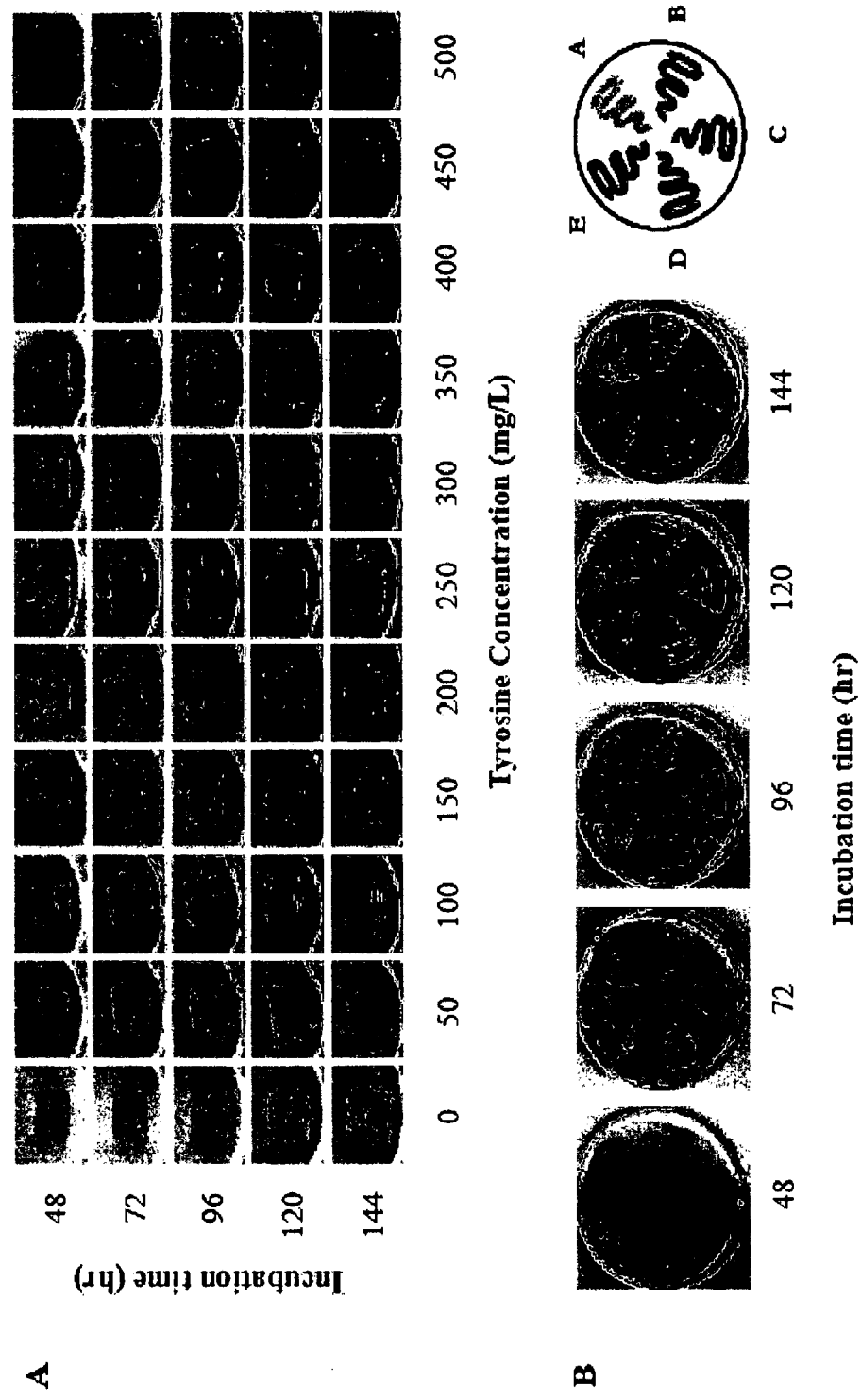
FIG. 5. Melanin production on MOPS-agar plates with 20 mM Na$_2$HPO$_4$. (A) Melanin production by K12 ΔpheA ΔtyrR pTrcmelA$^{mut1}$ with L-tyrosine supplementation. (B) Melanin production by five L-tyrosine production strains (Table 1). Image brightness and contrast were adjusted with Adobe Photoshop CS2 (Brightness +25; Contrast +45).

Since the high-throughput implementation of this assay will likely require use in a solid medium format, a series of experiments was conducted to determine whether incremental differences in melanin production could also be distinguished by visual inspection on agar plates. K12 ΔpheA ΔtyrR pTrcmelA$^{mut1}$ colonies were streaked on L-tyrosine-supplemented MOPS-agar plates and incubated at 30° C. for the specified periods of time. After 72 hours, plates with L-tyrosine concentrations differing by as low as 50 mg/L were easily differentiated based on both the intensity of pigmentation and the radial diffusion of melanin (FIG. 5A). The visual contrast between colonies became even more pronounced with increasing incubation times. These favorable trends were not just limited to externally supplemented L-tyrosine; a similar pigmentation pattern was observed among strains capable of different levels of L-tyrosine production (Table 1; A-E), with the highest L-tyrosine producer exhibiting the darkest coloration (FIG. 5B).

$Na_2HPO_4$ Supplementation Increases the Buffering Capacity of MOPS Minimal Medium To gain a better understanding of how $Na_2HPO_4$ exerts its effect on melanin synthesis, additional supplementation experiments were performed with the following chemicals: sodium chloride (NaCl), potassium phosphate (dibasic, $K_2HPO_4$), and sodium phosphate (monobasic, $NaH_2PO_4$). A proper basis for comparison was established by maintaining equivalent concentrations of sodium ($Na^+$) or phosphate ($HPO_4^{2-}$ or $H_2PO_4^-$) ions in all media formulations. The addition of NaCl to MOPS minimal medium had a slightly beneficial effect on melanin production but was only able to increase titers to 24-30% of the values observed with 20 mM $Na_2HPO_4$ (Table 3). Thus, the $Na^+$ concentration has only a marginal impact on melanin synthesis, and the bulk of the improvement in tyrosinase enzyme activity relies on the increase in $HPO_4^{2-}$ availability. In accordance with this hypothesis, high melanin titers were once again attained when $K_2HPO_4$, another source of $HPO_4^{2-}$, was added to the medium. Interestingly, the addition of $NaH_2PO_4$ did not have a significant effect on melanin production, suggesting that $Na_2HPO_4$ supplementation is needed simply to impart the medium with extra buffering capacity. Further evidence arises from an apparent correlation between culture pH and melanin titers, with the highest pH values (6.55-6.67) resulting in the greatest melanin titers. When a 50-50 mixture of $NaH_2PO_4$ and $Na_2HPO_4$ was added to the medium, intermediate values for both pH and melanin concentrations were observed (Table 3). These findings are consistent with other recent reports on R. etli MelA activity. Using a partially purified MelA tyrosinase, Cabrera-Valladares et al. found that the pH optimum for the enzyme's L-dopa oxidase activity lies in the range of 6.5-7.5 (8). Subsequent optimization of melanin production in stationary-phase E. coli revealed a pH optimum of 7.5 (15).

TABLE 3

Melanin production and pH of K12 ΔpheA ΔtyrR pTrcmelA$^{mut1}$ in MOPS minimal medium with supplementation$^a$

| | Melanin Production (mg/L) | | Culture pH | |
|---|---|---|---|---|
| Supplementation$^b$ | 72 hr | 96 hr | 72 hr | 96 hr |
| None | 24.6 | 36.8 | 4.60 | 4.57 |
| Sodium phosphate, dibasic (Na$_2$HPO$_4$)$^b$ | 305.0 | 401.4 | 6.57 | 6.55 |
| Sodium chloride (NaCl)$^c$ | 73.6 | 116.8 | 4.91 | 4.91 |
| Potassium phosphate, dibasic (K$_2$HPO$_4$)$^c$ | 302.7 | 391.8 | 6.65 | 6.67 |

TABLE 3-continued

Melanin production and pH of K12 ΔpheA ΔtyrR pTrcmelA$^{mut1}$ in MOPS minimal medium with supplementation[a]

|  | Melanin Production (mg/L) | | Culture pH | |
|---|---|---|---|---|
| Supplementation[b] | 72 hr | 96 hr | 72 hr | 96 hr |
| Sodium phosphate, monobasic (NaH$_2$PO$_4$)[c] | 21.8 | 33.6 | 4.74 | 4.76 |
| Sodium phosphate, monobasic and dibasic (NaH$_2$PO$_4$ + Na$_2$HPO$_4$)[c,d] | 84.6 | 135.5 | 5.04 | 5.04 |

[a]All cultures were supplemented with 500 mg/L L-tyrosine.
[b]Na$_2$HPO$_4$ was supplemented at a final concentration of 20 mM.
[c]For all other medium formulations, supplemented components were added such that the sodium (Na$^+$) or phosphate (HPO$_4^{2-}$ or H$_2$PO$_4^-$) ion concentrations were equivalent to those found in 20 mM Na$_2$HPO$_4$.
[d]NaH$_2$PO$_4$ and Na$_2$HPO$_4$ contributed equal amounts of HPO$_4^{2-}$ or H$_2$PO$_4^-$.

Figure 6:
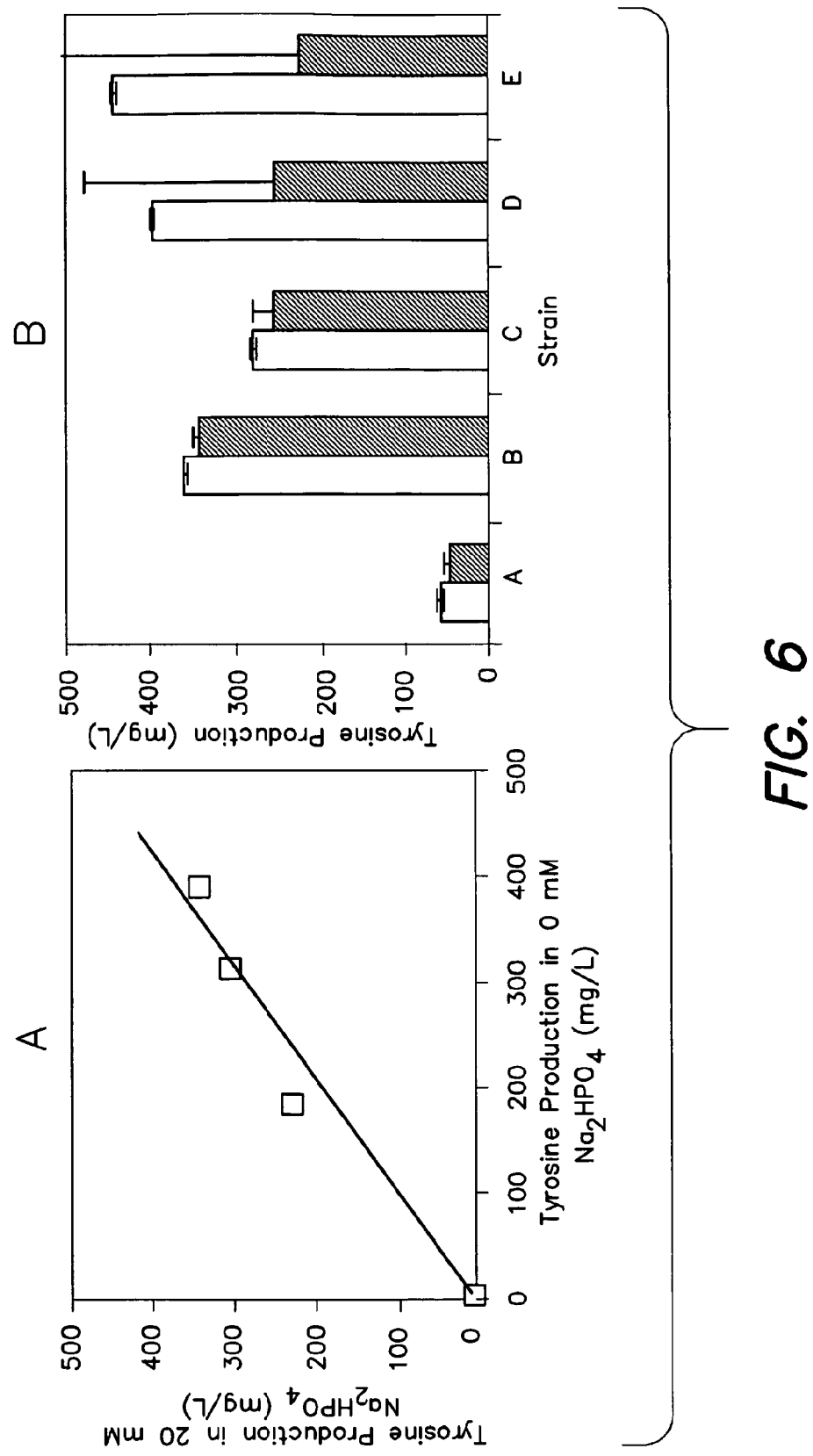
FIG. 6. Effect of cellular and cultivation perturbations on L-tyrosine production. (A) L-tyrosine production of Strains A, C, D, and E (Table 1) in 0 and 20 mM Na$_2$HPO$_4$. (B)

Effect of Na$_2$HPO$_4$ Supplementation and pTrcmelA$^{mut1}$ on L-Tyrosine Production During the course of developing of this assay, two major genotypic and environmental perturbations were introduced. Both the heterologous expression of the *R. etli* melA gene and the change in medium formulation (as necessitated by the Na$_2$HPO$_4$ requirement for melanin synthesis) have the potential to interfere with L-tyrosine production in the strains of interest. Thus, studies were conducted to elucidate what effects, if any, such alterations have on the behavior of these strains. To ensure that Na$_2$HPO$_4$ supplementation does not have a negative effect on L-tyrosine synthesis, the production levels of four strains (Table 1; A, C-E) were characterized in MOPS minimal medium containing 0 mM and 20 mM Na$_2$HPO$_4$. A plot of the concentrations achieved by these strains reveals that the overall trends in L-tyrosine production were maintained (FIG. 6A). It is therefore reasonable to assume that the strains exhibiting the greatest capacity for L-tyrosine production in 20 mM Na$_2$HPO$_4$ will remain the top performers under standard cultivation conditions. To determine the impact of expressing a heterologous tyrosinase, the production levels of five strains (Table 1; A-E) were measured both in the presence and absence of pTrcmelA$^{mut1}$. As seen in FIG. 6B, the presence of the reporter plasmid had an unfavorable effect on the final L-tyrosine titers for the top two production strains, D and E, when cultivated at 37° C. in liquid MOPS minimal medium. The L-tyrosine concentrations measured for these strains exhibited wide standard deviations, even for biological replicates within the same experiment. This demonstrates the importance of removing pTrcmelA$^{mut1}$ from strains identified through the melanin screen prior to a more rigorous quantification of L-tyrosine production through liquid cultivation and HPLC analysis.

Screening a Random Knockout Library

Taking these results altogether, we have developed a selection strategy for utilizing this assay to screen large combinatorial libraries of mutant strains (FIG. 7). In our initial application of the screen, a random knockout library was generated by the transposon-mediated mutagenesis of the parental strain K12 ΔpheA ΔtyrR pCL1920::tyrA$^{fbr}$aroG$^{fbr}$ pTrcmelA$^{mut1}$ (29). Following transformation with the pJA1 vector, the library was plated directly onto MOPS-agar supplemented with 20 mM Na$_2$HPO$_4$ and 0.4 μg/ml CuSO$_4$, providing the optimum conditions for the synthesis of melanin. The plates were incubated at 30° C. for a period of 120-144 hours during which colonies of noticeably different pigmentation intensities were detected. To achieve greater resolving power, the darkest colonies from this stage (165 colonies) were streaked out on a fresh set of MOPS-agar plates and incubated for an additional 120-144 hours. Subjecting strains through this second round of selection allowed us to more clearly differentiate between the levels of melanin produced by these isolates, as well as to limit further selection of false positives. Following this second incubation period, 30 strains exhibiting the most intense coloration underwent repeated rounds of subculturing in Amp$^-$ media to facilitate the loss of pTrcmelA$^{mut1}$, which was shown earlier to have a detrimental effect on final L-tyrosine titers. In most cases, the plasmid was easily lost after four rounds of reinoculation, with each round lasting at least five to six hours (data not shown). Individual clones were isolated and tested for growth on both Amp$^+$ and Amp$^-$ media to verify the loss of the plasmid, and ampicillin-sensitive mutants were then cultivated under standard L-tyrosine production conditions and analyzed by HPLC.

Out of an initial library size of 21,000 viable colonies, 30 mutants were chosen for a rigorous quantification of L-tyrosine production. Of these isolated strains, 2 mutants were found to possess L-tyrosine titers 57-71% above that of the parental strain (Table 4). The integrations were sequenced and verified to have occurred in the C-terminal region of the epsilon subunit of DNA polymerase III, encoded by dnaQ (30), and a small, 48 amino-acid hypothetical protein encoded by ygdT (31).

TABLE 4

L-tyrosine production of strains isolated from a random knockout library (24 hr)

| Strain | Genotype | L-tyrosine production (mg/L) | % increase above parental |
|---|---|---|---|
| D (parental) | K12 ΔpheA ΔtyrR pCL1920::tyrA$^{fbr}$aroG$^{fbr}$ | 347 | — |
| KO-dnaQ | K12 ΔpheA ΔtyrR dnaQ::kan pCL1920::tyrA$^{fbr}$aroG$^{fbr}$ | 545 | 57 |
| KO-ygdT | K12 ΔpheA ΔtyrR ygdT::kan pCL1920::tyrA$^{fbr}$aroG$^{fbr}$ | 594 | 71 |

DISCUSSION

Although the microbial production of aromatic amino acids, such as L-tyrosine, has been extensively studied and reviewed in recent years (5, 6, 11, 13, 24, 33), strategies for strain improvement have typically exhibited a narrow focus on well-characterized biochemical pathways and regulatory mechanisms. Combinatorial methods for metabolic engineering were previously of limited use due to the absence of a high-throughput screen for assessing the phenotype of interest. In this study, we have described the development of a simple high-throughput screen for the microbial production of L-tyrosine based on the synthesis of the dark pigment melanin. Although proof-of-concept experiments were carried out in *E. coli*, such a screen can be readily applied to any microorganism capable of expressing a tyrosinase enzyme with high activity towards L-tyrosine. Many bacteria, including several species of *Rhizobia*, *Streptomyces*, *Pseudomonas*, and *Bacilli* naturally express these enzymes and produce melanin for protection against UV damage and increased virulence and pathogenesis (8, 9, 18, 21, 25). Hence, such strains possess the innate ability to act as sensors for the production of L-tyrosine. Additionally, in cases where the host strain lacks an endogenous tyrosinase, the appropriate gene(s) can easily be introduced on a plasmid or integrated into the bacterial chromosome.

Screening for L-tyrosine production by monitoring melanin synthesis is a versatile technique that can be implemented in a variety of formats. Although the screening strategy presented here focuses on a solid medium implementation, liquid culture experiments can also be carried out in 96-well microtiter plates with individual strains from a combinatorial library inoculated into separate wells. After cultivation in media conducive for melanin production, the absorbance at 400 nm is measured, and desirable mutants are selected for further characterization. Although the described method suggests the use of the same strain for both L-tyrosine production and detection, it is also possible to decouple these two steps by creating a strain exclusively for detection. In such a screening strategy, mutants from a combinatorial library are first individually cultured in 96-well microtiter plates. After a set period of time, the culture supernatants, which contain different amounts of microbially-produced L-tyrosine, are then used as a growth medium component for a separate reporter strain expressing melA. Detection strains grown in the highest L-tyrosine concentrations will synthesize the most melanin and exhibit the highest absorbances at 400 nm, allowing for the identification of the best performing mutants. This latter strategy bears similarity to a recently published method for mevalonate detection with a GFP-expressing mevalonate auxotroph (19). This "biosensor," as it was termed, allows one to measure the mevalonate content of a culture by monitoring the growth or fluorescence of the auxotrophic reporter strain. Although such a technique can also be used for L-tyrosine production through the construction of the appropriate auxotroph, coupling L-tyrosine production with melanin synthesis has the added convenience of requiring only one culturing step to simultaneously produce and detect the compound of interest. This important feature also allows for the simple execution of this screen in a solid medium format, which can be used to further enhance the high-throughput nature of the assay. As described earlier, with this approach, combinatorial libraries are plated directly on MOPS-agar medium, and colonies that exhibit the darkest pigmentation are selected for further analysis. Such a technique precludes the need for expensive robotics to automate the selection and inoculation of colonies into microtiter plates and multi-plate scanners to increase the throughput of the absorbance measurements. Through this method, libraries on the order of $10^6$ in size can be probed with relative ease. Although the utility of the mevalonate biosensor strain was also demonstrated in a solid medium format by utilizing a plate spraying technique, this method was only shown to distinguish between mevalonate-producing and non-mevalonate-producing colonies (19). This approach would be particularly difficult to implement on agar plates for the case of L-tyrosine production, since the parental strain that is used to generate the combinatorial libraries already produces an elevated level of L-tyrosine. It is therefore likely that the most severe growth-limiting factor for the auxotrophic strain will be the depletion of a carbon source rather than L-tyrosine.

More recently, an alternative assay for L-tyrosine production has been described which utilizes a chemical reaction between 1-nitroso-2-naphthol and L-tyrosine to produce a yellow, fluorescent product. This method, which was originally developed for the determination of L-tyrosine levels in blood plasma (27), was adapted for the case of microbial L-tyrosine production in microtiter plates (32). Again, however, the high-throughput implementation of this assay is heavily reliant on the availability of expensive robotics to automate sampling, reaction preparations, and fluorescence measurements.

Screening a random knockout library with this melanin-based selection strategy has led to the discovery of two targets that were successful in eliciting significant increases in L-tyrosine production. A dnaQ::kan mutation in the background of the parental strain K12 ΔpheA ΔtyrR pCL1920:: tyrA$^{fbr}$aroG$^{fbr}$ led to a 57% increase in L-tyrosine production; a ygdT::kan mutation resulted in even further increases (71%). It is important to note that rational design approaches would not have been capable of predicting either of these genetic changes, particularly for the case of a ygdT deletion, which encodes for an as-yet unidentified hypothetical protein. Certainly, for both mutant strains identified, further work must be conducted to elucidate the complex relationship between genotype and cellular phenotype. This example, however, serves to illustrate the great potential that can be unlocked by such a screening strategy. Indeed, the application of this simple assay for probing a variety of combinatorial libraries will likely lead to the discovery of additional targets that were previously unreachable through traditional methods of metabolic engineering.

Example 2

Application of Screen Towards Identifying Transcriptional Mutants with Enhanced Capacities for L-Tyrosine Production Global transcription machinery engineering (gTME) has recently emerged as an effective diversification tool for a variety of strain improvement applications (2, 3, 28). As such, we decided to utilize our screen to assess the potential of such strategies for increasing L-tyrosine production in *E. coli*. Specifically, we constructed two separate gTME libraries— one based on the mutagenesis of the principal sigma factor in *E. coli* (rpoD) and the other based on altering the alpha subunit of the RNA polymerase holoenzyme (rpoA). Both proteins make sequence-specific contacts with DNA (−10, −35 promoter regions and upstream promoter elements, respectively) and have thus been implicated in altering the promoter specificity of the transcriptional machinery. Such alterations are expected to generate phenotypic diversity within a population through a complete reprogramming of the cellular transcriptome.

Libraries were constructed in the background of a pre-engineered parental strain exhibiting modest levels of L-tyrosine production: *E. coli* K12 ΔpheA tyrR::P$_{LtetO-1}$ tyrA$^{fbr}$aroG$^{fbr}$lacZ::P$_{LtetO-1}$tyrA$^{fbr}$aroG$^{fbr}$. Our screening protocol was then used to identify high L-tyrosine producers from these large combinatorial libraries (~$10^6$ colonies). Our search uncovered three mutant strains—rpoA14, rpoA27, and rpoD3—which exhibited L-tyrosine production levels between 77 and 113% above that of the parental strain (Table 5), once again demonstrating the utility of our screen for optimizing a L-tyrosine production phenotype.

TABLE 5

L-tyrosine production of strains isolated from two gTME libraries (48 hr)

| Strain | L-tyrosine production (mg/L) | % increase above parental |
| --- | --- | --- |
| parental | 418 | — |
| rpoA14 | 742 | 77 |
| rpoA27 | 806 | 92 |
| rpoD3 | 893 | 113 |

REFERENCES

1. Alper, H., K. Miyaoku, and G. Stephanopoulos. 2005. Construction of lycopene-overproducing *E. coli* strains by combining systematic and combinatorial gene knockout targets. Nat Biotechnol 23:612-6.
2. Alper, H., J. Moxley, E. Nevoigt, G. R. Fink, and G. Stephanopoulos. 2006. Engineering yeast transcription machinery for improved ethanol tolerance and production. Science 314:1565-8.
3. Alper, H., and G. Stephanopoulos. 2007. Global transcription machinery engineering: A new approach for improving cellular phenotype. Metab Eng. 9(3): 258-67.
4. Bailey, J. E. 1991. Toward a science of metabolic engineering. Science 252:1668-75.
5. Berry, A. 1996. Improving production of aromatic compounds in *Escherichia coli* by metabolic engineering. Trends in Biotechnology 14:250-256.
6. Bongaerts, J., M. Kramer, U. Muller, L. Raeven, and M. Wubbolts. 2001. Metabolic engineering for microbial production of aromatic amino acids and derived compounds. Metab Eng 3:289-300.
7. Bravo, A., and J. Mora. 1988. Ammonium Assimilation in *Rhizobium-Phaseoli* by the Glutamine Synthetase-Glutamate Synthase Pathway. Journal of Bacteriology 170:980-984.
8. Cabrera-Valladares, N., A. Martinez, S. Pinero, V. H. Lagunas-Munoz, R. Tinoco, R. de Anda, R. Vazquez-Duhalt, F. Bolivar, and G. Gosset. 2006. Expression of the melA gene from *Rhizobium etli* CFN42 in *Escherichia coli* and characterization of the encoded tyrosinase. Enzyme and Microbial Technology 38:772-779.
9. Claus, H., and H. Decker. 2006. Bacterial tyrosinases. Syst Appl Microbiol 29:3-14.
10. della-Cioppa, G., S. J. Garger, G. G. Sverlow, T. H. Turpen, and L. K. Grill. 1990. Melanin production in *Escherichia coli* from a cloned tyrosinase gene. Biotechnology (N Y) 8:634-8.
11. Flores, N., J. Xiao, A. Berry, F. Bolivar, and F. Valle. 1996. Pathway engineering for the production of aromatic compounds in *Escherichia coli*. Nature Biotechnology 14:620-623.
12. Gonzalez, V., P. Bustos, M. A. Ramirez-Romero, A. Medrano-Soto, H. Salgado, I. Hernandez-Gonzalez, J. C. Hernandez-Celis, V. Quintero, G. Moreno-Hagelsieb, L. Girard, O. Rodriguez, M. Flores, M. A. Cevallos, J. Collado-Vides, D. Romero, and G. Davila. 2003. The mosaic structure of the symbiotic plasmid of *Rhizobium etli* CFN42 and its relation to other symbiotic genome compartments. Genome Biot 4:R36.
13. Ikeda, M. 2006. Towards bacterial strains overproducing L-tryptophan and other aromatics by metabolic engineering. Appl Microbiol Biotechnol 69:615-26.
14. Jin, Y. S., and G. Stephanopoulos. 2007. Multi-dimensional gene target search for improving lycopene biosynthesis in *Escherichia coli*. Metab Eng.
15. Lagunas-Munoz, V. H., N. Cabrera-Valladares, F. Bolivar, G. Gosset, and A. Martinez. 2006. Optimum melanin production using recombinant *Escherichia coli*. J Appl Microbiol 101:1002-8.
16. Lutke-Eversloh, T., and G. Stephanopoulos. 2007. L:-Tyrosine production by deregulated strains of *Escherichia coli*. Appl Microbiol Biotechnol 75:103-10.
17. Neidhardt, F. C., P. L. Bloch, and D. F. Smith. 1974. Culture medium for enterobacteria. J Bacteriol 119:736-47.
18. Nosanchuk, J. D., and A. Casadevall. 2003. The contribution of melanin to microbial pathogenesis. Cell Microbiol 5:203-23.
19. Pfleger, B. F., D. J. Pitera, J. D. Newman, V. J. Martin, and J. D. Keasling. 2007. Microbial sensors for small molecules: development of a mevalonate biosensor. Metab Eng 9:30-8.
20. Qi, W. W., T. Vannelli, S. Breinig, A. Ben-Bassat, A. A. Gatenby, S. L. Haynie, and F. S. Sariaslani. 2007. Functional expression of prokaryotic and eukaryotic genes in *Escherichia coli* for conversion of glucose to p-hydroxystyrene. Metab Eng.
21. Ruan, L., W. He, J. He, M. Sun, and Z. Yu. 2005. Cloning and expression of mel gene from *Bacillus thuringiensis* in *Escherichia coli*. Antonie Van Leeuwenhoek 87:283-8.
22. Sambrook, J., E. F. Fritsch, and T. Maniatis. 1989. Molecular cloning: a laboratory manual, 2nd ed. Cold Spring Harbor Laboratory, Cold Spring Harbor, N.Y.
23. Sariaslani, F. S. 2007. Development of a Combined Biological and Chemical Process for Production of Industrial Aromatics from Renewable Resources. Annu Rev Microbiol.
24. Sprenger, G. A. 2007. From scratch to value: engineering *Escherichia coli* wild type cells to the production of L: -phenylalanine and other fine chemicals derived from chorismate. Appl Microbiol Biotechnol.
25. Wang, G., A. Aazaz, Z. Peng, and P. Shen. 2000. Cloning and overexpression of a tyrosinase gene mel from *Pseudomonas maltophila*. FEMS Microbiol Lett 185:23-7.
26. Udenfriend, S., and J. R. Cooper. 1952. The chemical estimation of tyrosine and tyramine. J Biol Chem 196:227-33.
27. Waalkes T. P. and S. Udenfriend. 1957. A fluorometric method for the estimation of tyrosine in plasma and tissues. J Lab Clin Med 50:733-6.
28. Klein-Marcuschamer, D. and G. Stephanopoulos. 2008. Assessing the potential of mutational strategies to elicit new phenotypes in industrial strains. Proc Natl Acad Sci USA, 105(7):2319-24.
29. Badarinarayana, V., P. W. Estep, 3rd, J. Shendure, J. Edwards, S. Tavazoie, F. Lam, and G. M. Church. 2001. Selection analyses of insertional mutants using subgenic-resolution arrays. Nat Biotechnol 19:1060-5.
30. Taft-Benz, S. A., and R. M. Schaaper. 1999. The C-terminal domain of dnaQ contains the polymerase binding site. J Bacteriol 181:2963-5.
31. Ecocyc: Encyclopedia of *Escherichia coli* K-12 Genes and Metabolism. (http://ecocyc.org/)
32. Lutke-Eversloh, T., and G. Stephanopoulos. 2007. A semi-quantitative high-throughput screening method for microbial L-tyrosine production in microtiter plates. J Ind Microbiol Biotechnol 34:807-811.
33. Lutke-Eversloh, T., C. N. S. Santos, and G. Stephanopoulos. 2007. Perspectives of biotechnological production of L-tyrosine and its applications. Appl Microbiol Biotechnol 77:751-62.

Other aspects of the invention will be clear to the skilled artisan and need not be repeated here. Each reference cited herein is incorporated by reference in its entirety for the relevant teaching contained therein.

The terms and expressions that have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for identifying bacterial strains that produce L-tyrosine, comprising:
   culturing in a medium one or more bacterial strains capable of L-tyrosine production and which heterologously express a tyrosinase, wherein the tyrosinase comprises the amino acid sequence of SEQ ID NO: 4, and wherein the tyrosinase has the ability to convert L-tyrosine into melanin, and
   determining the amount of melanin produced by the one or more bacterial strains, wherein production of melanin by a strain indicates that the strain produces L-tyrosine.

2. The method of claim 1, wherein the amount of melanin produced by the one or more bacterial strains correlates positively with the amount of L-tyrosine produced by the one or more bacterial strains.

3. The method of claim 1, wherein the amount of melanin produced by the one or more bacterial strains is detected by a visual method or a spectrophotometric method.

4. The method of claim 1, wherein the pH of the culture medium is at least about 5.

5. A method for identifying bacterial strains that produce extracellular L-tyrosine, comprising:
   culturing a reporter bacterial strain that heterologously expresses a tyrosinase in a sample of a culture medium in which one or more bacterial strains capable of producing extracellular L-tyrosine are being cultured or have been cultured, wherein the tyrosinase comprises the amino acid sequence of SEQ ID NO: 4, and wherein the tyrosinase has the ability to convert L-tyrosine into melanin, and
   determining the amount of melanin produced by the reporter strain, wherein production of melanin by a reporter strain indicates that the one or more bacterial strains produces extracellular L-tyrosine.

6. The method of claim 5, wherein the amount of melanin produced by the reporter strain correlates positively with the amount of L-tyrosine produced by the one or more bacterial strains.

7. The method of claim 5, wherein the amount of melanin produced by the reporter strain is detected by a visual method or a spectrophotometric method.

8. The method of claim 5, wherein the pH of the culture medium is at least about 5.

* * * * *

SEQUENCE LISTING

<160> NUMBER OF SEQ ID NOS: 6

<210> SEQ ID NO 1
<211> LENGTH: 1830
<212> TYPE: DNA
<213> ORGANISM: Rhizobium etli

<400> SEQUENCE: 1

```
ttgccgtggc tggtcggcaa gccgtcgctc gaacgatcat ggaatgcgat actaagtttt      60
ccggaatctg gattccaact ggaatgcagg aatacgatcg gtagtagcgt ttttagctcg     120
cattttacgc tgcattttcg agtggcacgt cgcttgcttc atttctcgtg ccgccgattc     180
accgaaactc agaaagagcc aacgcaagct ctatggtggt gcgaattgcc cactgctccc     240
gcgcccagac ggcgcggaac cggcctaaaa gcggcattaa tcttggcgaa ggacaattca     300
aatccaaggg agagtaagat gagcatcaca cgcagacatg tcatcgttca gggtggcgtc     360
attgcagcag gcctgctcgc cagcggccta ccggggacaa aagccttcgc gcagataccg     420
tcaatccctt ggcggcgctc actgcagggc ttggcctgga acgacccgat catcgagacc     480
tatcgcgacg cagtgcgcct tctcaacgcc cttcccgcca gcgacaaatt caactgggtc     540
aacctctcga aaattcacgg cagcggtgac gtcgtcaaat actgcccgca tggcaactgg     600
tatttcctgc cgtggcacag ggcctatacg gctatgtacg agcgcatcgt tcggcacgtg     660
accaagaaca acgatttcgc tatgccgttc tgggactgga ccgacaatcc gtacctgccc     720
gaagtgttca caatgcaaaa gacgcccgac ggcaaggaca atccacttta tgtttcgtcg     780
cgcacctggc caatcacgca gccgatgccg gacaatatag ttgggccaca ggttctcaac     840
accatcctaa cggcgaagcc atacgaggtc ttcggcacca cccgcccgga gggacagaac     900
tcactcgatc cttcctgggt caccaccagc agcggcacgc agggggcgct ggaatacaca     960
ccgcacaatc aggtgcacaa caatatcggt ggctggatgc cggaaatgtc gtcgccccgc    1020
gatccgatct tcttcatgca tcattgcaac atcgaccgca tctgggcgac ctggaatttg    1080
cgcaacgcca acagcacgga tcgactctgg gccgacatgc cgttcaccga caatttctac    1140
gatgtcgacg gcaacttctg gtccccgaag gtctctgacc tttatgttcc agaggaactc    1200
ggatacaatt atggtttccg gacctacttc aaggtcgcgg cggcgagcgc caaaacgctg    1260
gccctgaacg ataaactcac gtccgtgatc gcggcgacgg cgaccgatgc tgcaatcgcc    1320
ggcgtgacga ccacctccac ggacaacagc aaggcggcaa cggaaaacgt gccgcttttcg    1380
ctgccgatca agatcccggc gggcgcattg caggagatcg tccgccaacc gcctctgcca    1440
tccggcatgg atacaatgga tttcggcgcg gcacaggagc aggcggcctc cgctcctcgt    1500
gtgctggcat tcctgcgcga tgtcgagatc accagtgcca gcacgaccag cgttcgggtg    1560
tttctcggca agaacgacct taaggccgat acgcccgtca ccgatcccca ttacgtcggt    1620
tctttcgccg ttctcggtca tgacggcgac catcatcgca aaccatcctt cgtcctcgat    1680
ctgacggacg cgatccagcg ggtttacggc ggaaggggc agacggatgg cgaggccatc    1740
gacctgcagc tcattcctgt cggatcggga gcggcaaac ccggcgccgt agagcccgca    1800
aagctagaaa tagccatagt gtccgcctaa                                     1830
```

<210> SEQ ID NO 2
<211> LENGTH: 609
<212> TYPE: PRT
<213> ORGANISM: Rhizobium etli

<400> SEQUENCE: 2

-continued

```
Met Pro Trp Leu Val Gly Lys Pro Ser Leu Glu Arg Ser Trp Asn Ala
1               5                   10                  15
Ile Leu Ser Phe Pro Glu Ser Gly Phe Gln Leu Glu Cys Arg Asn Thr
            20                  25                  30
Ile Gly Ser Ser Val Phe Ser Ser His Phe Thr Leu His Phe Arg Val
        35                  40                  45
Ala Arg Arg Leu Leu His Phe Ser Cys Arg Arg Phe Thr Glu Thr Gln
    50                  55                  60
Lys Glu Pro Thr Gln Ala Leu Trp Trp Cys Glu Leu Pro Thr Ala Pro
65                  70                  75                  80
Ala Pro Arg Arg Gly Thr Gly Leu Lys Ala Ala Leu Ile Leu Ala
                85                  90                  95
Lys Asp Asn Ser Asn Pro Arg Glu Ser Lys Met Ser Ile Thr Arg Arg
            100                 105                 110
His Val Ile Val Gln Gly Gly Val Ile Ala Ala Gly Leu Leu Ala Ser
            115                 120                 125
Gly Leu Pro Gly Thr Lys Ala Phe Ala Gln Ile Pro Ser Ile Pro Trp
    130                 135                 140
Arg Arg Ser Leu Gln Gly Leu Ala Trp Asn Asp Pro Ile Ile Glu Thr
145                 150                 155                 160
Tyr Arg Asp Ala Val Arg Leu Leu Asn Ala Leu Pro Ala Ser Asp Lys
                165                 170                 175
Phe Asn Trp Val Asn Leu Ser Lys Ile His Gly Ser Gly Asp Val Val
            180                 185                 190
Lys Tyr Cys Pro His Gly Asn Trp Tyr Phe Leu Pro Trp His Arg Ala
            195                 200                 205
Tyr Thr Ala Met Tyr Glu Arg Ile Val Arg His Val Thr Lys Asn Asn
    210                 215                 220
Asp Phe Ala Met Pro Phe Trp Asp Trp Thr Asp Asn Pro Tyr Leu Pro
225                 230                 235                 240
Glu Val Phe Thr Met Gln Lys Thr Pro Asp Gly Lys Asp Asn Pro Leu
                245                 250                 255
Tyr Val Ser Ser Arg Thr Trp Pro Ile Thr Gln Pro Met Pro Asp Asn
            260                 265                 270
Ile Val Gly Pro Gln Val Leu Asn Thr Ile Leu Thr Ala Lys Pro Tyr
            275                 280                 285
Glu Val Phe Gly Thr Thr Arg Pro Glu Gly Gln Asn Ser Leu Asp Pro
    290                 295                 300
Ser Trp Val Thr Thr Ser Ser Gly Thr Gln Gly Ala Leu Glu Tyr Thr
305                 310                 315                 320
Pro His Asn Gln Val His Asn Asn Ile Gly Gly Trp Met Pro Glu Met
                325                 330                 335
Ser Ser Pro Arg Asp Pro Ile Phe Phe Met His His Cys Asn Ile Asp
            340                 345                 350
Arg Ile Trp Ala Thr Trp Asn Leu Arg Asn Ala Asn Ser Thr Asp Arg
            355                 360                 365
Leu Trp Ala Asp Met Pro Phe Thr Asp Asn Phe Tyr Asp Val Asp Gly
    370                 375                 380
Asn Phe Trp Ser Pro Lys Val Ser Asp Leu Tyr Val Pro Glu Glu Leu
385                 390                 395                 400
Gly Tyr Asn Tyr Gly Phe Arg Thr Tyr Phe Lys Val Ala Ala Ala Ser
                405                 410                 415
```

```
Ala Lys Thr Leu Ala Leu Asn Asp Lys Leu Thr Ser Val Ile Ala Ala
            420                 425                 430
Thr Ala Thr Asp Ala Ala Ile Ala Gly Val Thr Thr Ser Thr Asp
        435                 440                 445
Asn Ser Lys Ala Ala Thr Glu Asn Val Pro Leu Ser Leu Pro Ile Lys
        450                 455                 460
Ile Pro Ala Gly Ala Leu Gln Glu Ile Val Arg Gln Pro Pro Leu Pro
465                 470                 475                 480
Ser Gly Met Asp Thr Met Asp Phe Gly Ala Gln Glu Gln Ala Ala
                485                 490                 495
Ser Ala Pro Arg Val Leu Ala Phe Leu Arg Asp Val Glu Ile Thr Ser
        500                 505                 510
Ala Ser Thr Thr Ser Val Arg Val Phe Leu Gly Lys Asn Asp Leu Lys
        515                 520                 525
Ala Asp Thr Pro Val Thr Asp Pro His Tyr Val Gly Ser Phe Ala Val
        530                 535                 540
Leu Gly His Asp Gly Asp His His Arg Lys Pro Ser Phe Val Leu Asp
545                 550                 555                 560
Leu Thr Asp Ala Ile Gln Arg Val Tyr Gly Gly Arg Gly Gln Thr Asp
                565                 570                 575
Gly Glu Ala Ile Asp Leu Gln Leu Ile Pro Val Gly Ser Gly Ala Gly
                580                 585                 590
Lys Pro Gly Ala Val Glu Pro Ala Lys Leu Glu Ile Ala Ile Val Ser
        595                 600                 605
Ala

<210> SEQ ID NO 3
<211> LENGTH: 1830
<212> TYPE: DNA
<213> ORGANISM: Rhizobium etli

<400> SEQUENCE: 3
atggcgtggc tggtcggcaa gccgtcgctc gaacgatcat ggaatgcgat actaagtttt      60
ccggaatctg gattccaact ggaatgcagg aatacgatcg gtagtagcgt ttttagctcg     120
cattttacgc tgcattttcg agtggcacgt cgcttgcttc atttctcgtg ccgccgattc     180
accgaaactc agaagagcc aacgcaagct ctatggtggt gcgaattgcc cactgctccc     240
gcgcccagac ggcgcggaac cggcctaaaa gcggcattaa tcttggcgaa ggacaattca     300
aatccaaggg agagtaagat gagcatcaca cgcagacatg tcatcgttca gggtggcgtc     360
attgcagcag gcctgctcgc cagcggccta ccggggacaa aagccttcgc gcagataccg     420
tcaatccctt ggcggcgctc actgcagggc ttggcctgga cgacccgat catcgagacc     480 tatcgcgacg cagtgcgcct tctcaacgcc cttccgcca gcgacaaatt caactgggtc     540
aacctctcga aaattcacgg cagcggtgac gtcgtcaaat actgcccgca tggcaactgg     600
tatttcctgc cgtggcacag ggcctatacg gctatgtacg agcgcatcgt tcggcacgtg     660
accaagaaca acgatttcgc tatgccgttc tgggactgga ccgacaatcc gtacctgccc     720
gaagtgttca caatgcaaaa gacgcccgac ggcaaggaca tccacttta tgtttcgtcg     780 cgcacctggc caatcacgca gccgatgccg acaatatag ttgggccaca ggttctcaac     840
accatcctaa cggcgaagcc atacgaggtc ttcggcacca cccgccccga gggacagaac     900
tcactcgatc cttcctgggt caccaccagc agcggcacgc agggggcgct ggaatacaca     960
ccgcacaatc aggtgcacaa caatatcggt ggctggatgt cggaaatgtc gtcgccccgc    1020
```

```
gatccgatct tcttcatgca tcattgcaac atcgaccgca tctgggcgac ctggaatttg    1080
cgcaacgcca acagcacgga tcgactctgg gccgacatgc cgttcaccga caatttctac    1140
gatgtcgacg gcaacttctg gtccccgaag gtctctgacc tttatgttcc agaggaactc    1200
ggatacaatt atggtttccg gacctacttc aaggtcgcgg cggcgagcgc caaaacgctg    1260
gccctgaacg ataaactcac gtccgtgatc gcggcgacgg cgaccgatgc tgcaatcgcc    1320
ggcgtgacga ccacctccac ggacaacagc aaggcggcaa cggaaaacgt gccgctttcg    1380
ctgccgatca agatcccggc gggcgcattg caggagatcg tccgccaacc gcctctgcca    1440
tccggcatgg atacaatgga tttcggcgcg gcacaggagc aggcggcctc cgctcctcgt    1500
gtgctggcat tcctgcgcga tgtcgagatc accagtgcca gcacgaccag cgttcgggtg    1560
tttctcggca agaacgacct taaggccgat acgcccgtca ccgatcccca ttacgtcggt    1620
tctttcgccg ttctcggtca tgacggcgac catcatcgca aaccatcctt cgtcctcgat    1680
ctgacggacg cgatccagcg ggtttacggc ggaaggggc agacggatgg cgaggccatc    1740
gacctgcagc tcattcctgt cggatcggga gcgggcaaac ccggcgccgt agagcccgca    1800
aagctagaaa tagccatagt gtccgcctaa                                    1830
```

<210> SEQ ID NO 4
<211> LENGTH: 609
<212> TYPE: PRT
<213> ORGANISM: Rhizobium etli

<400> SEQUENCE: 4

```
Met Pro Trp Leu Val Gly Lys Pro Ser Leu Glu Arg Ser Trp Asn Ala
1               5                   10                  15

Ile Leu Ser Phe Pro Glu Ser Gly Phe Gln Leu Glu Cys Arg Asn Thr
            20                  25                  30

Ile Gly Ser Ser Val Phe Ser Ser His Phe Thr Leu His Phe Arg Val
        35                  40                  45

Ala Arg Arg Leu Leu His Phe Ser Cys Arg Arg Phe Thr Glu Thr Gln
    50                  55                  60

Lys Glu Pro Thr Gln Ala Leu Trp Trp Cys Glu Leu Pro Thr Ala Pro
65                  70                  75                  80

Ala Pro Arg Arg Arg Gly Thr Gly Leu Lys Ala Ala Leu Ile Leu Ala
                85                  90                  95

Lys Asp Asn Ser Asn Pro Arg Glu Ser Lys Met Ser Ile Thr Arg Arg
            100                 105                 110

His Val Ile Val Gln Gly Gly Val Ile Ala Ala Gly Leu Leu Ala Ser
        115                 120                 125

Gly Leu Pro Gly Thr Lys Ala Phe Ala Gln Ile Pro Ser Ile Pro Trp
    130                 135                 140

Arg Arg Ser Leu Gln Gly Leu Ala Trp Asn Asp Pro Ile Ile Glu Thr
145                 150                 155                 160

Tyr Arg Asp Ala Val Arg Leu Leu Asn Ala Leu Pro Ala Ser Asp Lys
                165                 170                 175

Phe Asn Trp Val Asn Leu Ser Lys Ile His Gly Ser Gly Asp Val Val
            180                 185                 190

Lys Tyr Cys Pro His Gly Asn Trp Tyr Phe Leu Pro Trp His Arg Ala
        195                 200                 205

Tyr Thr Ala Met Tyr Glu Arg Ile Val Arg His Val Thr Lys Asn Asn
    210                 215                 220
```

```
Asp Phe Ala Met Pro Phe Trp Asp Trp Thr Asp Asn Pro Tyr Leu Pro
225                 230                 235                 240

Glu Val Phe Thr Met Gln Lys Thr Pro Asp Gly Lys Asp Asn Pro Leu
            245                 250                 255

Tyr Val Ser Ser Arg Thr Trp Pro Ile Thr Gln Pro Met Pro Asp Asn
        260                 265                 270

Ile Val Gly Pro Gln Val Leu Asn Thr Ile Leu Thr Ala Lys Pro Tyr
    275                 280                 285

Glu Val Phe Gly Thr Thr Arg Pro Glu Gly Gln Asn Ser Leu Asp Pro
290                 295                 300

Ser Trp Val Thr Thr Ser Ser Gly Thr Gln Gly Ala Leu Glu Tyr Thr
305                 310                 315                 320

Pro His Asn Gln Val His Asn Asn Ile Gly Gly Trp Met Ser Glu Met
            325                 330                 335

Ser Ser Pro Arg Asp Pro Ile Phe Phe Met His His Cys Asn Ile Asp
        340                 345                 350

Arg Ile Trp Ala Thr Trp Asn Leu Arg Asn Ala Asn Ser Thr Asp Arg
    355                 360                 365

Leu Trp Ala Asp Met Pro Phe Thr Asp Asn Phe Tyr Asp Val Asp Gly
370                 375                 380

Asn Phe Trp Ser Pro Lys Val Ser Asp Leu Tyr Val Pro Glu Glu Leu
385                 390                 395                 400

Gly Tyr Asn Tyr Gly Phe Arg Thr Tyr Phe Lys Val Ala Ala Ala Ser
            405                 410                 415

Ala Lys Thr Leu Ala Leu Asn Asp Lys Leu Thr Ser Val Ile Ala Ala
        420                 425                 430

Thr Ala Thr Asp Ala Ala Ile Ala Gly Val Thr Thr Thr Ser Thr Asp
    435                 440                 445

Asn Ser Lys Ala Ala Thr Glu Asn Val Pro Leu Ser Leu Pro Ile Lys
450                 455                 460

Ile Pro Ala Gly Ala Leu Gln Glu Ile Val Arg Gln Pro Pro Leu Pro
465                 470                 475                 480

Ser Gly Met Asp Thr Met Asp Phe Gly Ala Ala Gln Glu Gln Ala Ala
            485                 490                 495

Ser Ala Pro Arg Val Leu Ala Phe Leu Arg Asp Val Glu Ile Thr Ser
        500                 505                 510

Ala Ser Thr Thr Ser Val Arg Val Phe Leu Gly Lys Asn Asp Leu Lys
    515                 520                 525

Ala Asp Thr Pro Val Thr Asp Pro His Tyr Val Gly Ser Phe Ala Val
530                 535                 540

Leu Gly His Asp Gly Asp His His Arg Lys Pro Ser Phe Val Leu Asp
545                 550                 555                 560

Leu Thr Asp Ala Ile Gln Arg Val Tyr Gly Arg Gly Gln Thr Asp
            565                 570                 575

Gly Glu Ala Ile Asp Leu Gln Leu Ile Pro Val Gly Ser Gly Ala Gly
        580                 585                 590

Lys Pro Gly Ala Val Glu Pro Ala Lys Leu Glu Ile Ala Ile Val Ser
    595                 600                 605

Ala

<210> SEQ ID NO 5
<211> LENGTH: 25
<212> TYPE: DNA
<213> ORGANISM: Rhizobium etli
```

```
<400> SEQUENCE: 5
taaaccatgg cgtggctggt cggca                                          25

<210> SEQ ID NO 6
<211> LENGTH: 39
<212> TYPE: DNA
<213> ORGANISM: Rhizobium etli

<400> SEQUENCE: 6
acgaagcttt taggcggaca ctatggctat ttctagctt                           39
```